(12) United States Patent
Wang et al.

(10) Patent No.: US 6,824,781 B2
(45) Date of Patent: Nov. 30, 2004

(54) METHOD OF IMPAIRING MOVEMENT OF A CLA + MEMEORY T-CELL WITHIN OR TO THE SKIN OF A MAMMAL BY ADMINISTERING A CTACK ANTAGONIST

(75) Inventors: Wei Wang, Palo Alto, CA (US); Elizabeth R. Oldham, Mountain View, CA (US); Hortensia Soto, Sunnyvale, CA (US); Ying Liu, Mountain View, CA (US); Susan A. Hudak, Redwood City, CA (US); Bernhard Homey, Palo Alto, CA (US); Janine M. Morales, San Francisco, CA (US); Sirid-Aimee Kellermann, Palo Alto, CA (US); Leslie M. McEvoy, Mountain View, CA (US); Edward P. Bowman, San Carlos, CA (US); Albert Zlotnik, Palo Alto, CA (US)

(73) Assignee: Schering Corporation, Kenilworth, NJ (US)

(*) Notice: Subject to any disclaimer, the term of this patent is extended or adjusted under 35 U.S.C. 154(b) by 0 days.

(21) Appl. No.: 09/898,751

(22) Filed: Jul. 2, 2001

(65) Prior Publication Data

US 2002/0160024 A1 Oct. 31, 2002

Related U.S. Application Data

(63) Continuation-in-part of application No. 09/471,549, filed on Dec. 23, 1999, now abandoned.
(60) Provisional application No. 60/136,570, filed on May 27, 1999, and provisional application No. 60/113,868, filed on Dec. 24, 1998.

(51) Int. Cl.$^7$ .................. A61K 39/395; C07K 16/24
(52) U.S. Cl. .................. 424/158.1; 424/130.1; 514/2; 530/387.1
(58) Field of Search .................. 435/4, 7.1, 325, 435/375; 514/2, 12; 424/85.1, 198.1, 130.1; 530/300, 350, 351, 387.1

(56) References Cited

U.S. PATENT DOCUMENTS 5,665,345 A 9/1997 Yarchoan et al. .......... 424/85.2

FOREIGN PATENT DOCUMENTS

WO WO 98/23750 6/1998

OTHER PUBLICATIONS

Kakinuma et al. Increased serum cutaneous T cell–attracting chemokine (CCL27) levels in patients with atopic dermatitis and psoriasis vulgaris. J Allergy Clin Immunol 111: 592–597, 2003.*
Gillitzer et al. Chemokines in cutaneous wound healing. J Leukocyte Biol 69: 513–521, 2001.*
Tannock and Hill. The Basic Science of Oncology, New York: McGraw–Hill, 1998, pp. 430–431, 495.*
Kirby et al. Successful treatment of severe recalcitrant psoriasis with combination infliximal and methotrexate. Clin Dermatol 26: 27–29, 2001.*
Keating et al. Infliximab, an updated review of its use in Chrohn's disease and rheumatoid arthritis. Biodrugs 16(2): 111–148, 2002.*
Elliot et al. Treatment of rheumatoid arthritis with chimeric monoclonal antibodies to tumor necrosis factor alpha. Arthritis Rheumatism 36(12): 1681–1690, 1993.*
Moreland et al. Treatment of rheumatoid arthritis with a recombinant human tumor necrosis factor receptor (p75)–fusion protein. New Eng J Med 337(3): 141–147, 1997.*
Bondeson et al. Tumour necrosis factor as a therapeutic target in rheumatoid arthritis and other chronic inflammatory diseases: the clinical experience with infliximab. Int J Clin Pract 55(3): 211–216, 2001.*
Reiss et al. CC chemokine receptor (CCR)4 and the CCR10 ligand cutaneous T cell–attracting chemokine (CTACK) in lymphocyte trafficking to inflamed skin. J Exp Med 194(10): 1541–1547, 2001.*
Kunkel et al. Chemokines and the tissue–specific migration of lymphocytes. Immunity 16: 1–4, 2002.*
Homey et al. CCL27–CCR10 interactions regulate T cell–mediated skin inflammation. Nature Medicine 8(2): 157–165, 2002.*
M. Marra, et al., *GenBank*, Accession No. AA023970, Jan. 21, 1997. Definition: "mh95f08.r1 Soares mouse placenta 4NbMP13.5 14.5 *Mus musculus* cDNA clone Image:458727 5'similar to SW:GPR2_Human P46092 Probable G Protein–Coupled Receptor GPR2. [1] ;, mRNA sequence."
Kouji Matsushima & Joost J. Oppenheim, *Cytokine* 1:2–13, Nov. 1989. "Interleukin 8 and MCAF: Novel Inflammatory Cytokines Inducible By IL 1 and TNF".
Catherine J. McMahan, et al., *EMBO Journal*, 10(10):2821–2832, 1991. "A novel IL–1 receptor, cloned from B cells by mammalian expression, is expressed in many cell types".
Michael D. Miller, et al., *Proc. Natl. Acad. Sci., USA* 89:2950–2954, 1992. "The human cytokine I–309 is a monocyte chemoattractant".
Janine Morales, et al., *Proc. Natl. Acad. Sci., USA*, 96(25):14470–14475, Dec. 7, 1999. "CTACK, a skin–associated chemokine that preferentially attracts skin–homing memory t cells".
Joost J. Oppenheim, et al., *Ann. Rev. Immunol.* 9:617–648, 1991. "Properties of the Novel Proinflammatory Supergene 'Intercrine' Cytokine Family".

(List continued on next page.)

*Primary Examiner*—Elizabeth Kemmerer
*Assistant Examiner*—Bridget E. Bunner

(57) ABSTRACT

Agonists or antagonists of CTACK or Vic chemokines, and various methods of use in dermatological and related applications are provided. In particular, the method makes use of fact that the CTACK or Vic chemokines are specifically capable of inducing movement of a skin cell subset. Moreover, matching of ligand with GPR2 receptor in mammals provides methods of use.

13 Claims, No Drawings

OTHER PUBLICATIONS

Paul Proost, et al., *J. Leukoc. Biol.* 59:67–74, Jan. 1996. "Human monocyte chemotactic proteins–2 and –3: structural and functional comparison with MCP–1".

Carol J. Raport, et al., *J. Leukoc. Biol.* 59:18–23, Jan. 1996. "New members of the chemokine receptor gene family".

Devora L. Rossi, et al., *J. Immunology*, 158(3):1033–1036, Feb. 1997. "Identification Through Bioinformatics of Two New Macrophage Proinflamitory Human Chemokines MIP–3α, MIP–3β[1,2]".

Michel Samson, et al., *Biochemistry* 35:3362–3367, 1996. "Molecular Cloning and Functional Expression of a New Human CC–Chemokine Receptor Gene".

Roger A. Sayle and E. James Milner–White, *TIBS*, 20:374–376, Sep. 1995. "RASMOL: biomolecular graphics for all".

Thomas J. Schall, in *The Cytokine Handbook*, 2nd ed., Academic Press Ltd., NY, pp 419–460, 1994. "The Chemokines".

Thomas J. Schall, et al., *Curr. Opin. Immunol.* 6:865–873, 1994. "Chemokines, leukocyte trafficking, and inflammation".

Thomas J. Schall, *Cytokine* 3:165–183, May 1991. "Biology of the Rantes/Sis Cytokine Family".

Thomas J. Schall, et al., in *The Chemokines*, Plenum Press, NY, pp 29–37, 1993. "Receptor/Ligand Interactions in the C–C Chemokine Family".

Bernhard Homey, et al., *Journal of Immunology*, 164:3465–3470, Apr. 1, 2000. "Cutting Edge The Orphan Chemokine Receptor G Protein–Coupled Receptor–2 (GPR–2, CCR10) Binds the Skin–Associated Chemokine CCL27 (CTACK/ALP/ILC)".

R. Horuk, et al., *J. Leukoc. Biol.* 59:29–38, Jan. 1996. "The Duffy antigen receptor for chemokines: structural analysis and expression in the brain".

Richard Horuk, *TIPS* 15:159–165, May 1994. "Molecular properties of the chemokine receptor family".

Richard Horuk, *Immunol. Today* 15:169–174, 1994. "The interleukin–8–receptor family: from chemokines to malaria".

Toshio Imai, et al., *J. Biol. Chem.*, 272(23):15036–15042, 1997. "The T Cell–directed CC Chemokine TARC Is a Highly Specific Biological Ligand for CC Chemokine Receptor 4".

Izuni Ishikawa–Mochizuki, et al., *FEBS Letters*, 460(3):544–548, Nov. 5, 1999. Molecular cloning of a novel CC chemokine, interleukin–11 receptor α–locus chemokine (ILC), which is located on chromosome 9p13 and a potential homologue of a CC chemokine encoded by molluscum contagiosum virus.

David J. Kelvin, et al., *J. Leukoc. Biol.* 54:604–612, Dec. 1993. "Chemokines and serpentines: the molecular biology of chemokine receptors".

Fang Liao, et al., *Biochem. Biophys. Res. Commun.*, 236:212–217, 1997. "STRL22 Is a Receptor for the CC Chemokine MIP–3α".

Fang Liao, et al., *J. Immunology*, 162:186–194, 1999. "CC–Chemokine Receptor 6 Is Expressed on Diverse Memory Subsets of T Cells and Determines Responsiveness to Macrophage Inflammatory Protein–3α".

Patricia J. Lodi, et al., *Science* 263:1762–1767, Mar. 25, 1994. "High–Resolution Structure of the β Chemokine hMIP–1β by Multidimensional NMR".

Adriano Marchese, et al., *Genomics*, 23(3):609–618, 1994. "Cloning of Human Genes Encoding Novel G Protein–Coupled Receptors".

A. Marchese, et al.,*GenBank*, Accession No. U13667, L35537, Apr. 1, 1995. Definition "Human G proteincoupled receptor (GPR2) gene, partial cds."

M. Marra, et al., *GenBank*, Accession No. AA930619, Apr. 23, 1998. Definition: "vy67b03.r1 Stratagene mouse macrophage (#937306) *Mus musculus* cDNA clone Image:1311245 5' similar to SW:GPR2_Human P46092 Probable G Protein–Coupled Receptor GPR2.; mRNA sequence."

M. Marra, et al., *GenBank*, Accession No. AA871520, Mar. 16, 1998. Definition. "vq36e07.r1 Barstead bowel MPLRB9 *Mus musculus* cDNA clone Image:1096356 5' similar to SW:GPR2_Human P46092 Probable G Protein–Receptor GPR2. ;, mRNA sequence."

Sunil K. Ahuja, et al., *Immunol. Today* 15:281–287, 1994. "Chemokine receptors and molecular mimicry".

Ghalig Alkatib, et al., *Science* 272:1955–1958, Jun. 28, 1996. "CC CKR5: A RANTES, MIP–1α, MIP–1β Receptor as a Fusion Cofactor for Macorphage–Tropic HIV–1".

Masataka Baba, et al., *J. Biological Chemistry*, 272(23):14893–14898, Jun. 6, 1997. "Identification of CCR6, the Specific Receptor for a Novel Lymphocyte–directed CC Chemokine LARC".

Kevin B. Bacon, et al., *Int. Arch. Allergy Immunol.* 109:97–109, 1996. "Chemokines as Mediators of Allergic Inflammation".

Michael Balter, *Science* 272:1740, Jun. 21, 1996. "A Second Coreceptor for HIV in Early Stages of Infection".

Ian Clark–Lewis, et al., *J. Leukoc. Biol.* 57:703–711, 1995. "Structure–activity relationships of chemokines".

HongKui Deng, et al., *Nature* 381:661–666, Jun. 20, 1996. "Identification of a major co–receptor for primary isolates of HIV–1".

Tatjana Dragic, et al., *Nature* 381:667–673, Jun. 20, 1996. "HIV entry into CD4+ cells is mediated by the chemokine receptor CC–CKR–5".

Tobias Doerks, et al., *TIG*, 14(6):248–250, Jun. 1998. "Protein annotation: detective work for funtion prediction".

David P. Gearing, et al.,*Embo Journal*, 8(12):3667–3676, 1989. "Expression cloning of a receptor for human granulocyte–macrophage colony–stimulation factor".

David R Greaves, et al., *J. Exp. Med.*, 186(6):837–844, Sep. 15, 1997. "CCR6, a CC Chemokine Receptor that Interacts with Macrophage Iflammatory Protein 3α and Is Highly Expressed in Human Dendritic Cell".

Angela M. Groneborn, et al., *Prot. Engg.* 4:263–269, 1991. "Modeling the three–dimensional structure of the monocyte chemo–attractant and activating protein MCAF/MCP–1 on the basis of the solution structure of interleukin–8".

Kunio Hieshima, et al., *J. Biological Chemistry*, 272(9):5846–5853, Feb. 28, 1997. "Molecular Cloning of a Novel Human CC Chemokine Liver and Activation–regulated Chemokine (LARC) Expressed in Liver".

Stephen J. O'Brien and Michael Dean *Scientific American*, 277:44–52, Sep. 1997. "In Search of AIDS–Resistance Genes".

Bahram Bodaghi et al.,*J. Exp. Med.*, 188 (5): 855–866, Sep. 1998. "Chemokine Sequestration by Viral Chemoreceptors as a Novel Escape Strategy: Withdrawl of Chemokines from the Environment of Cytomegalovirus–infected Cells".

Adriano Marchese, et al. *Genomics.*, 23:609–618, Jul. 1994. "Cloning of Human Genes Encoding Novel G Protein-Coupled Receptors".

Mark Y. Stoeckle, et al., *The New Biologist* 2:313–323, Apr. 1990. "Two Burgeoning Families of Platelet Factor 4–Related Proteins: Mediators of the Inflammatory Response".

Robert M. Strieter, et al., *J. Inv. Med.* 42:640–651, Dec. 1994. "Acute Lung Injury: The Role of Cytokines in the Elicitation of Neutrophils".

Robert M. Strieter, et al., *J. Leukoc. Biol.* 57:752–762, May 1995. "Role of C–X–C chemokines as regulators of angiogenesis in lung cancer".

Angus W. Thompson, Ed., *The Cytokine Handbook*, 2nd ed., The Academic Press Inc.; San Diego, CA, 1994.

Alain P. Vicari, et al., *J. Allergy Clin. Immun.*, 99(1) part 2:S246, Abstract 1003, Jan. 1997. "TECK: a novel CC Chemokine associated with T–cell development".

Alain P. Vicari, et al., *Immunity*, 7:291–301, Aug. 1997. "TECK: a Novel CC Chemokine Specifically Expressed by Thymic Dendritic Cells and Potentially Involved in T Cell Development".

Ulrich O. Wenzel and Hanna E. Abboud, *Am. J. Kidney Diseases* 26:982–994, Dec. 1995. "Chemokines and Renal Disease".

Ryu Yoshida, et al., *J. Biological Chemistry*, 272(21):13803–13809, May 23, 1997. "Molecular Cloning of a Novel Human CC Chemokine EBI1–ligand Chemokine That Is a Specific Functional Ligand for EBI1, CCR7".

Osamu Yoshie, et al., *J. Leukocyte Biology*, 62(5):634–644, Nov. 1997. "Novel lymphocyte–specific CC chemokines and their receptors".

Angel Zaballos, et al., *Biochem Biophys. Res. Comm.*, 227(3):846–853, Oct. 1996. "Molecular Cloning and RNA Expression of Two New Human Chemokine Receptor–like Genes".

Alfred Garzino–Demo, et al., *Journal of Clinical Immunology*, 18 (4):243–255, Mar. 1998. "Chemokine Receptors and Chemokines in HIV Infection".

George A. Donzella. et al., *Nature Medicine*, 4 (1) 72–77, Jan. 1998. "AMD3100, a small molecule inhibitor of HIV–1 entry via the CXCR4 co–receptor".

Dominique Schols, et al. *J. Exp. Med.*, 186 (8): 1383–1388, Oct. 1997. "Inhibition of T tropic HIV Strains by Selective Antagonization of the Chemokine Receptor CXCR4".

Dominique Schols, et al. *Jounral of Virology*, 72 (5): 4032–4037, May 1998. "T Cell Line Tropic Human Immunodeficiency Virus Type 1 that is Made Resistant to Stromal Cell–Derived Factor 1α Contains Mutations in the Envelope gp120 but does not show a switch in Coreceptor Use".

Beatrice Labrosse, et al., *Journal of Virology*, 72 (8): 6381–6388. Aug. 1998. "Determinants for Sensitivity of Human Immunodeficiency Virus Coreceptor CXCR4 to the Bicyclam AMD3100".

Christopher C. Broder and Ronald G. Collman, *J. of Leukocyte Biology*, 62: 20–29 Jul. 1997. Chemokine receptors and HIV.

Joanna F. Berson and Robert W. Doms, *Immunology*, 10: 237–248, 1998. "Structure function studies of the HIV–1 coreceptors".

* cited by examiner

SEQUENCE LISTING

<160> NUMBER OF SEQ ID NOS: 16

<210> SEQ ID NO 1
<211> LENGTH: 1089
<212> TYPE: DNA
<213> ORGANISM: Homo sapiens
<220> FEATURE:
<221> NAME/KEY: CDS
<222> LOCATION: (1)..(1086)
<223> OTHER INFORMATION:

<400> SEQUENCE: 1

```
atg ggg acg gag gtt tta gag cag gtt tcc tgg ggc cat tac tct ggg      48
Met Gly Thr Glu Val Leu Glu Gln Val Ser Trp Gly His Tyr Ser Gly
1               5                   10                  15 gat gaa gag gac gca tac tcg gct gag cca ctg ccg gag ctt tgc tac      96
Asp Glu Glu Asp Ala Tyr Ser Ala Glu Pro Leu Pro Glu Leu Cys Tyr
                20                  25                  30 aag gcc gat gtc cag gcc ttc agc cgg gcc ttc caa ccc agt gtc tcc     144
Lys Ala Asp Val Gln Ala Phe Ser Arg Ala Phe Gln Pro Ser Val Ser
            35                  40                  45 ctg acg ctg gct gcg ctg ggt ctg gcc ggc aat ggc ctg gtc ctg gcc     192
Leu Thr Leu Ala Ala Leu Gly Leu Ala Gly Asn Gly Leu Val Leu Ala
        50                  55                  60
```

```
acc cac ctg gca gcc cga cgc gca gcg cgc tcg ccc acc tct gcc cac      240
Thr His Leu Ala Ala Arg Arg Ala Ala Arg Ser Pro Thr Ser Ala His
 65              70              75              80 ctg ctc cag ctg gcc ctg gcc gac ctc ttg ctg gcc ctg act ctg ccc      288
Leu Leu Gln Leu Ala Leu Ala Asp Leu Leu Leu Ala Leu Thr Leu Pro
             85              90              95 ttc gcg gca gca ggg gct ctt cag ggc tgg agt ctg gga agt gcc acc      336
Phe Ala Ala Ala Gly Ala Leu Gln Gly Trp Ser Leu Gly Ser Ala Thr
            100             105             110 tgc cgc acc atc tct ggc ctc tac tcg gcc tcc ttc cac gcc ggc ttc      384
Cys Arg Thr Ile Ser Gly Leu Tyr Ser Ala Ser Phe His Ala Gly Phe
            115             120             125 ctc ttc ctg gcc tgt atc agc gcc gac cgc tac gtg gcc atc gcg cga      432
Leu Phe Leu Ala Cys Ile Ser Ala Asp Arg Tyr Val Ala Ile Ala Arg
130             135             140 gcg ctc cca gcc ggg ccg cgg ccc tcc act ccc ggc cgc gca cac ttg      480
Ala Leu Pro Ala Gly Pro Arg Pro Ser Thr Pro Gly Arg Ala His Leu
145             150             155             160 gtc tcc gtc atc gtg tgg ctg ctg tca ctg ctc ctg gcg ctg cct gcg      528
Val Ser Val Ile Val Trp Leu Leu Ser Leu Leu Leu Ala Leu Pro Ala
                165             170             175 ctg ctc ttc agc cag gat ggg cag cgg gaa ggc caa cga cgc tgt cgc      576
Leu Leu Phe Ser Gln Asp Gly Gln Arg Glu Gly Gln Arg Arg Cys Arg
            180             185             190 ctc atc ttc ccc gag ggc ctc acg cag acg gtg aag ggg gcg agc gcc      624
Leu Ile Phe Pro Glu Gly Leu Thr Gln Thr Val Lys Gly Ala Ser Ala
            195             200             205 gtg gcg cag gtg gcc ctg ggc ttc gcg ctg ccg ctg ggc gtc atg gta      672
Val Ala Gln Val Ala Leu Gly Phe Ala Leu Pro Leu Gly Val Met Val
            210             215             220 gcc tgc tac gcg ctt ctg ggc cgc acg ctg ctg gcc gcc agg ggg ccc      720
Ala Cys Tyr Ala Leu Leu Gly Arg Thr Leu Leu Ala Ala Arg Gly Pro
225             230             235             240 gag cgc cgg cgt gcg ctg cgc gtc gtg gtg gct ctg gtg gcg gcc ttc      768
Glu Arg Arg Arg Ala Leu Arg Val Val Val Ala Leu Val Ala Ala Phe
            245             250             255 gtg gtg ctg cag ctg ccc tac agc ctc gcc ctg ctg gat act gcc        816
Val Val Leu Gln Leu Pro Tyr Ser Leu Ala Leu Leu Leu Asp Thr Ala
            260             265             270 gat cta ctg gct gcg cgc gag cgg agc tgc cct gcc agc aaa cgc aag      864
Asp Leu Leu Ala Ala Arg Glu Arg Ser Cys Pro Ala Ser Lys Arg Lys
            275             280             285 gat gtc gca ctg ctg gtg acc agc ggc ttg gcc ctc gcc cgc tgt ggc      912
Asp Val Ala Leu Leu Val Thr Ser Gly Leu Ala Leu Ala Arg Cys Gly
290             295             300 ctc aat ccc gtt ctc tac gcc ttc ctg ggc ctg cgc ttc cgc cag gac      960
Leu Asn Pro Val Leu Tyr Ala Phe Leu Gly Leu Arg Phe Arg Gln Asp
305             310             315             320 ctg cgg agg ctg cta cgg ggt ggg agc tcg ccc tca ggg cct caa ccc     1008
Leu Arg Arg Leu Leu Arg Gly Gly Ser Ser Pro Ser Gly Pro Gln Pro
            325             330             335 cgc cgc ggc tgc ccc cgc cgg ccc cgc ctt tct tcc tgc tca gct ccc     1056
Arg Arg Gly Cys Pro Arg Arg Pro Arg Leu Ser Ser Cys Ser Ala Pro
            340             345             350 acg gag acc cac agt ctc tcc tgg gac aac tag                         1089
Thr Glu Thr His Ser Leu Ser Trp Asp Asn
            355             360
```

<210> SEQ ID NO 2
<211> LENGTH: 362

```
<212> TYPE: PRT
<213> ORGANISM: Homo sapiens

<400> SEQUENCE: 2

Met Gly Thr Glu Val Leu Glu Gln Val Ser Trp Gly His Tyr Ser Gly
 1               5                  10                  15

Asp Glu Glu Asp Ala Tyr Ser Ala Glu Pro Leu Pro Glu Leu Cys Tyr
             20                  25                  30

Lys Ala Asp Val Gln Ala Phe Ser Arg Ala Phe Gln Pro Ser Val Ser
         35                  40                  45

Leu Thr Leu Ala Ala Leu Gly Leu Ala Gly Asn Gly Leu Val Leu Ala
 50                  55                  60

Thr His Leu Ala Ala Arg Arg Ala Ala Arg Ser Pro Thr Ser Ala His
 65                  70                  75                  80

Leu Leu Gln Leu Ala Leu Ala Asp Leu Leu Leu Ala Leu Thr Leu Pro
                 85                  90                  95

Phe Ala Ala Gly Ala Leu Gln Gly Trp Ser Leu Gly Ser Ala Thr
                100                 105                 110

Cys Arg Thr Ile Ser Gly Leu Tyr Ser Ala Ser Phe His Ala Gly Phe
             115                 120                 125

Leu Phe Leu Ala Cys Ile Ser Ala Asp Arg Tyr Val Ala Ile Ala Arg
130                 135                 140

Ala Leu Pro Ala Gly Pro Arg Pro Ser Thr Pro Gly Arg Ala His Leu
145                 150                 155                 160

Val Ser Val Ile Val Trp Leu Leu Ser Leu Leu Leu Ala Leu Pro Ala
                165                 170                 175

Leu Leu Phe Ser Gln Asp Gly Gln Arg Glu Gly Gln Arg Arg Cys Arg
                180                 185                 190

Leu Ile Phe Pro Glu Gly Leu Thr Gln Thr Val Lys Gly Ala Ser Ala
             195                 200                 205

Val Ala Gln Val Ala Leu Gly Phe Ala Leu Pro Leu Gly Val Met Val
210                 215                 220

Ala Cys Tyr Ala Leu Leu Gly Arg Thr Leu Leu Ala Ala Arg Gly Pro
225                 230                 235                 240

Glu Arg Arg Arg Ala Leu Arg Val Val Ala Leu Val Ala Ala Phe
             245                 250                 255

Val Val Leu Gln Leu Pro Tyr Ser Leu Ala Leu Leu Leu Asp Thr Ala
             260                 265                 270

Asp Leu Leu Ala Ala Arg Glu Arg Ser Cys Pro Ala Ser Lys Arg Lys
             275                 280                 285

Asp Val Ala Leu Leu Val Thr Ser Gly Leu Ala Leu Ala Arg Cys Gly
         290                 295                 300

Leu Asn Pro Val Leu Tyr Ala Phe Leu Gly Leu Arg Phe Arg Gln Asp
305                 310                 315                 320

Leu Arg Arg Leu Leu Arg Gly Gly Ser Ser Pro Ser Gly Pro Gln Pro
                325                 330                 335

Arg Arg Gly Cys Pro Arg Arg Pro Arg Leu Ser Ser Cys Ser Ala Pro
             340                 345                 350

Thr Glu Thr His Ser Leu Ser Trp Asp Asn
             355                 360

<210> SEQ ID NO 3
<211> LENGTH: 1089
<212> TYPE: DNA
<213> ORGANISM: Mus musculus
```

<220> FEATURE:
<221> NAME/KEY: CDS
<222> LOCATION: (1)..(1086)
<223> OTHER INFORMATION:

<400> SEQUENCE: 3

```
atg ggg acc aag ccc aca gag cag gtc tcc tgg gga ctt tac tcc ggg       48
Met Gly Thr Lys Pro Thr Glu Gln Val Ser Trp Gly Leu Tyr Ser Gly
1               5                   10                  15 tac gat gag gag gcc tat tcg gtt ggg ccg ctg cca gag ctc tgt tac       96
Tyr Asp Glu Glu Ala Tyr Ser Val Gly Pro Leu Pro Glu Leu Cys Tyr
            20                  25                  30 aag gct gat gtc cag gct ttc agt cgg gcc ttc caa ccc agt gtc tcc      144
Lys Ala Asp Val Gln Ala Phe Ser Arg Ala Phe Gln Pro Ser Val Ser
        35                  40                  45 ctg atg gtg gct gta ctg ggt ctg gct ggc aat ggc cta gtc ttg gcc      192
Leu Met Val Ala Val Leu Gly Leu Ala Gly Asn Gly Leu Val Leu Ala
    50                  55                  60 acc cat ctg gca gcc aga cga act acc cga tct ccc acc tcc gtt cac      240
Thr His Leu Ala Ala Arg Arg Thr Thr Arg Ser Pro Thr Ser Val His
65                  70                  75                  80 ctc ctc cag ttg gcc ctg gct gac ctt tta ttg gcc ctg act ttg cct      288
Leu Leu Gln Leu Ala Leu Ala Asp Leu Leu Leu Ala Leu Thr Leu Pro
                85                  90                  95 ttt gct gca gca ggg gct ctt cag ggc tgg aat cta gga agt acc acc      336
Phe Ala Ala Ala Gly Ala Leu Gln Gly Trp Asn Leu Gly Ser Thr Thr
            100                 105                 110 tgc cgt gcc atc tca ggc ctc tac tcg gcc tct ttc cac gct ggc ttc      384
Cys Arg Ala Ile Ser Gly Leu Tyr Ser Ala Ser Phe His Ala Gly Phe
        115                 120                 125 ctc ttc cta gcc tgt atc agc gcc gac cgc tat gtg gcc atc gca cga      432
Leu Phe Leu Ala Cys Ile Ser Ala Asp Arg Tyr Val Ala Ile Ala Arg
    130                 135                 140 gct ctc cca gcc ggg cag cgg ccc tca acg cct agc cga gcg cac ttg      480
Ala Leu Pro Ala Gly Gln Arg Pro Ser Thr Pro Ser Arg Ala His Leu
145                 150                 155                 160 gtt tca gtc ttc gtg tgg ctg ttg gcg ctg ttt ctg gct cta cct gcg      528
Val Ser Val Phe Val Trp Leu Leu Ala Leu Phe Leu Ala Leu Pro Ala
                165                 170                 175 ctc ctt ttc agc cgg gac ggg cca cgt gaa ggc caa cga cgc tgt cgg      576
Leu Leu Phe Ser Arg Asp Gly Pro Arg Glu Gly Gln Arg Arg Cys Arg
            180                 185                 190 ctc att ttt ccc gaa agc ctc acg cag act gtg aaa ggg gca agc gca      624
Leu Ile Phe Pro Glu Ser Leu Thr Gln Thr Val Lys Gly Ala Ser Ala
        195                 200                 205 gtg gcg cag gtg gtc ctc ggc ttc gcg ctc cct ctg ggc gtc atg gca      672
Val Ala Gln Val Val Leu Gly Phe Ala Leu Pro Leu Gly Val Met Ala
    210                 215                 220 gcc tgt tat gcg ctc ctg ggc cgc acg ctt ctg gcc gcc agg ggg cca      720
Ala Cys Tyr Ala Leu Leu Gly Arg Thr Leu Leu Ala Ala Arg Gly Pro
225                 230                 235                 240 gag cgg cgg cgt gca ctg cgc gtc gtg gtg gct ttg gtg gtg gcc ttc      768
Glu Arg Arg Arg Ala Leu Arg Val Val Val Ala Leu Val Val Ala Phe
                245                 250                 255 gtg gtg ctg cag ttg ccc tac agc ctt gcc ctg ctg gat aca gcc          816
Val Val Leu Gln Leu Pro Tyr Ser Leu Ala Leu Leu Asp Thr Ala
            260                 265                 270 gat cta ctg gca gcc cgc gag cgg agc tgc tcc tcc agc aag cgc aag      864
Asp Leu Leu Ala Ala Arg Glu Arg Ser Cys Ser Ser Ser Lys Arg Lys
        275                 280                 285
```

-continued

```
gat cta gct ttg ctg gtc acc ggc ggc ttg acc ctg gtc cgt tgc agc      912
Asp Leu Ala Leu Leu Val Thr Gly Gly Leu Thr Leu Val Arg Cys Ser
    290                 295                 300 ctc aat ccg gtg ctt tat gcc ttt ttg ggc ctg cgt ttc cgc gga gac      960
Leu Asn Pro Val Leu Tyr Ala Phe Leu Gly Leu Arg Phe Arg Arg Asp
305                 310                 315                 320 ctg cgg agg ctg ctc cag ggc gga gga tgc agc ccg aag ccc aac cct      1008
Leu Arg Arg Leu Leu Gln Gly Gly Gly Cys Ser Pro Lys Pro Asn Pro
                325                 330                 335 cgt ggc cgc tgc ccc cgt cga ctc cgc ctt tct tcc tgc tct gct cct      1056
Arg Gly Arg Cys Pro Arg Arg Leu Arg Leu Ser Ser Cys Ser Ala Pro
            340                 345                 350 act gag acc cac agt ctc tct tgg gac aac tag                          1089
Thr Glu Thr His Ser Leu Ser Trp Asp Asn
        355                 360

<210> SEQ ID NO 4
<211> LENGTH: 362
<212> TYPE: PRT
<213> ORGANISM: Mus musculus

<400> SEQUENCE: 4

Met Gly Thr Lys Pro Thr Glu Gln Val Ser Trp Gly Leu Tyr Ser Gly
1               5                   10                  15

Tyr Asp Glu Glu Ala Tyr Ser Val Gly Pro Leu Pro Glu Leu Cys Tyr
            20                  25                  30

Lys Ala Asp Val Gln Ala Phe Ser Arg Ala Phe Gln Pro Ser Val Ser
        35                  40                  45

Leu Met Val Ala Val Leu Gly Leu Ala Gly Asn Gly Leu Val Leu Ala
    50                  55                  60

Thr His Leu Ala Ala Arg Arg Thr Thr Arg Ser Pro Thr Ser Val His
65                  70                  75                  80

Leu Leu Gln Leu Ala Leu Ala Asp Leu Leu Ala Leu Thr Leu Pro
                85                  90                  95

Phe Ala Ala Ala Gly Ala Leu Gln Gly Trp Asn Leu Gly Ser Thr Thr
            100                 105                 110

Cys Arg Ala Ile Ser Gly Leu Tyr Ser Ala Ser Phe His Ala Gly Phe
        115                 120                 125

Leu Phe Leu Ala Cys Ile Ser Ala Asp Arg Tyr Val Ala Ile Ala Arg
    130                 135                 140

Ala Leu Pro Ala Gly Gln Arg Pro Ser Thr Pro Ser Arg Ala His Leu
145                 150                 155                 160

Val Ser Val Phe Val Trp Leu Leu Ala Leu Phe Leu Ala Leu Pro Ala
                165                 170                 175

Leu Leu Phe Ser Arg Asp Gly Pro Arg Glu Gly Gln Arg Arg Cys Arg
            180                 185                 190

Leu Ile Phe Pro Glu Ser Leu Thr Gln Thr Val Lys Gly Ala Ser Ala
        195                 200                 205

Val Ala Gln Val Val Leu Gly Phe Ala Leu Pro Leu Gly Val Met Ala
    210                 215                 220

Ala Cys Tyr Ala Leu Leu Gly Arg Thr Leu Leu Ala Ala Arg Gly Pro
225                 230                 235                 240

Glu Arg Arg Arg Ala Leu Arg Val Val Ala Leu Val Val Ala Phe
                245                 250                 255

Val Val Leu Gln Leu Pro Tyr Ser Leu Ala Leu Leu Leu Asp Thr Ala
            260                 265                 270
```

-continued

```
Asp Leu Leu Ala Ala Arg Glu Arg Ser Cys Ser Ser Lys Arg Lys
        275                 280                 285

Asp Leu Ala Leu Leu Val Thr Gly Gly Leu Thr Leu Val Arg Cys Ser
    290                 295                 300

Leu Asn Pro Val Leu Tyr Ala Phe Leu Gly Leu Arg Phe Arg Arg Asp
305                 310                 315                 320

Leu Arg Arg Leu Leu Gln Gly Gly Cys Ser Pro Lys Pro Asn Pro
                325                 330                 335

Arg Gly Arg Cys Pro Arg Arg Leu Arg Leu Ser Ser Cys Ser Ala Pro
                340                 345                 350

Thr Glu Thr His Ser Leu Ser Trp Asp Asn
            355                 360
```

<210> SEQ ID NO 5
<211> LENGTH: 731
<212> TYPE: DNA
<213> ORGANISM: Homo sapiens
<220> FEATURE:
<221> NAME/KEY: CDS
<222> LOCATION: (56)..(436)
<223> OTHER INFORMATION:
<221> NAME/KEY: mat_peptide
<222> LOCATION: (122)..()
<223> OTHER INFORMATION:
<221> NAME/KEY: misc_feature
<222> LOCATION: (529)..(529)
<223> OTHER INFORMATION: unknown amino; may be "A", "C", or "G"

<400> SEQUENCE: 5

```
ggctgatcga acagcctcac ttgtgttgct gtcagtgcca gtagggcagg cagga atg    58
                                                             Met cag cag aga gga ctc gcc atc gtg gcc ttg gct gtc tgt gcg gcc cta   106
Gln Gln Arg Gly Leu Ala Ile Val Ala Leu Ala Val Cys Ala Ala Leu
    -20                 -15                 -10 cat gcc tca gaa gcc ata ctt ccc att gcc tcc agc tgt tgc acg gag   154
His Ala Ser Glu Ala Ile Leu Pro Ile Ala Ser Ser Cys Cys Thr Glu
 -5          -1  1                   5                       10 gtt tca cat cat att tcc aga agg ctc ctg gaa aga gtg aat atg tgt   202
Val Ser His His Ile Ser Arg Arg Leu Leu Glu Arg Val Asn Met Cys
             15                  20                  25 cgc atc cag aga gct gat ggg gat tgt gac ttg gct gct gtc atc ctt   250
Arg Ile Gln Arg Ala Asp Gly Asp Cys Asp Leu Ala Ala Val Ile Leu
         30                  35                  40 cat gtc aag cgc aga aga atc tgt gtc agc ccg cac aac cat act gtt   298
His Val Lys Arg Arg Arg Ile Cys Val Ser Pro His Asn His Thr Val
     45                  50                  55 aag cag tgg atg aaa gtg caa gct gcc aag aaa aat ggt aaa gga aat   346
Lys Gln Trp Met Lys Val Gln Ala Ala Lys Lys Asn Gly Lys Gly Asn
 60                  65                  70                  75 gtt tgc cac agg aag aaa cac cat ggc aag agg aac agt aac agg gca   394
Val Cys His Arg Lys Lys His His Gly Lys Arg Asn Ser Asn Arg Ala
                 80                  85                  90 cat cag ggg aaa cac gaa aca tac ggc cat aaa act cct tat            436
His Gln Gly Lys His Glu Thr Tyr Gly His Lys Thr Pro Tyr
                 95                 100                 105 tagagagtct acagataaat ctacagagac aattcctcaa gtggacttgg ccatgattgg   496
ttgtcctgca tactgatgaa actactgatg tcvgctggtc tgaaaggacc taccagaagc   556
taaatctcca agaatgccat ttccctatcc ctaatgattc aatctccctt accctgacca   616
atcagtggcc caaattttcc agcccctgc ctcccagaac cccagcccag aactcttcag   676
```

```
                                                       -continued
agatttaaga atctcctcct acctcctgac tcagccccat gtaatcatta aactc           731

<210> SEQ ID NO 6
<211> LENGTH: 127
<212> TYPE: PRT
<213> ORGANISM: Homo sapiens
<220> FEATURE:
<221> NAME/KEY: misc_feature
<222> LOCATION: (529)..(529)
<223> OTHER INFORMATION: unknown amino; may be "A", "C", or "G"

<400> SEQUENCE: 6

Met Gln Gln Arg Gly Leu Ala Ile Val Ala Leu Ala Val Cys Ala Ala
        -20                 -15                 -10

Leu His Ala Ser Glu Ala Ile Leu Pro Ile Ala Ser Ser Cys Cys Thr
     -5              -1   1               5                    10

Glu Val Ser His His Ile Ser Arg Arg Leu Leu Glu Arg Val Asn Met
                 15                  20                  25

Cys Arg Ile Gln Arg Ala Asp Gly Asp Cys Asp Leu Ala Ala Val Ile
             30                  35                  40

Leu His Val Lys Arg Arg Ile Cys Val Ser Pro His Asn His Thr
             45                  50                  55

Val Lys Gln Trp Met Lys Val Gln Ala Ala Lys Lys Asn Gly Lys Gly
 60                  65                  70

Asn Val Cys His Arg Lys Lys His His Gly Lys Arg Asn Ser Asn Arg
 75              80                  85                  90

Ala His Gln Gly Lys His Glu Thr Tyr Gly His Lys Thr Pro Tyr
                 95                  100                 105

<210> SEQ ID NO 7
<211> LENGTH: 543
<212> TYPE: DNA
<213> ORGANISM: Homo sapiens
<220> FEATURE:
<221> NAME/KEY: CDS
<222> LOCATION: (1)..(492)
<223> OTHER INFORMATION:

<400> SEQUENCE: 7 atg tcg cga ttg agg aga tac gag gtg gcg ctg gaa gcg gag gag gag      48
Met Ser Arg Leu Arg Arg Tyr Glu Val Ala Leu Glu Ala Glu Glu Glu
 1               5                  10                  15 atc tac tgg ggc tgc ttc tac ttt ttt cct tgg ctg cga atg tgg cgc      96
Ile Tyr Trp Gly Cys Phe Tyr Phe Phe Pro Trp Leu Arg Met Trp Arg
             20                  25                  30 agg gag cgg agt ccg atg tct cca aca agc cag aga cta agt ctg gaa     144
Arg Glu Arg Ser Pro Met Ser Pro Thr Ser Gln Arg Leu Ser Leu Glu
         35                  40                  45 gcc ccc agc ctc cca ctg aga agc tgg cat ccg tgg aac aag act aag     192
Ala Pro Ser Leu Pro Leu Arg Ser Trp His Pro Trp Asn Lys Thr Lys
 50                  55                  60 cag aag caa gaa gcc ttg cct ctg ccc tcc agc act agc tgc tgt act     240
Gln Lys Gln Glu Ala Leu Pro Leu Pro Ser Ser Thr Ser Cys Cys Thr
 65                  70                  75                  80 cag ctc tat aga cag cca ctc cca agc agg ctg ctg agg agg att gtc     288
Gln Leu Tyr Arg Gln Pro Leu Pro Ser Arg Leu Leu Arg Arg Ile Val
                 85                  90                  95 cac atg gaa ctg cag gag gcc gat ggg gac tgt cac ctc cag gct gtc     336
His Met Glu Leu Gln Glu Ala Asp Gly Asp Cys His Leu Gln Ala Val
             100                 105                 110 gtg ctt cac ctg gct cgg cgc agt gtc tgt gtt cat ccc cag aac cgc     384
```

-continued

```
Val Leu His Leu Ala Arg Arg Ser Val Cys Val His Pro Gln Asn Arg
        115                 120                 125 agc ctg gct cgg tgg tta gaa cgc caa ggg aaa agg ctc caa ggg act        432
Ser Leu Ala Arg Trp Leu Glu Arg Gln Gly Lys Arg Leu Gln Gly Thr
    130                 135                 140 gta ccc agt tta aat ctg gta cta caa aag aaa atg tac tca aac ccc        480
Val Pro Ser Leu Asn Leu Val Leu Gln Lys Lys Met Tyr Ser Asn Pro
145                 150                 155                 160 caa cag caa aac taataaagca acattagacg acaaaaaaaa aaaaaaaaa            532
Gln Gln Gln Asn aaaaaaaaa a                                                            543
```

<210> SEQ ID NO 8
<211> LENGTH: 164
<212> TYPE: PRT
<213> ORGANISM: Homo sapiens

<400> SEQUENCE: 8

```
Met Ser Arg Leu Arg Arg Tyr Glu Val Ala Leu Glu Ala Glu Glu Glu
1               5                   10                  15

Ile Tyr Trp Gly Cys Phe Tyr Phe Pro Trp Leu Arg Met Trp Arg
                20                  25                  30

Arg Glu Arg Ser Pro Met Ser Pro Thr Ser Gln Arg Leu Ser Leu Glu
            35                  40                  45

Ala Pro Ser Leu Pro Leu Arg Ser Trp His Pro Trp Asn Lys Thr Lys
        50                  55                  60

Gln Lys Gln Glu Ala Leu Pro Leu Pro Ser Ser Thr Ser Cys Cys Thr
65                  70                  75                  80

Gln Leu Tyr Arg Gln Pro Leu Pro Ser Arg Leu Leu Arg Ile Val
                85                  90                  95

His Met Glu Leu Gln Glu Ala Asp Gly Asp Cys His Leu Gln Ala Val
                100                 105                 110

Val Leu His Leu Ala Arg Arg Ser Val Cys Val His Pro Gln Asn Arg
        115                 120                 125

Ser Leu Ala Arg Trp Leu Glu Arg Gln Gly Lys Arg Leu Gln Gly Thr
    130                 135                 140

Val Pro Ser Leu Asn Leu Val Leu Gln Lys Lys Met Tyr Ser Asn Pro
145                 150                 155                 160

Gln Gln Gln Asn
```

<210> SEQ ID NO 9
<211> LENGTH: 393
<212> TYPE: DNA
<213> ORGANISM: Mus musculus
<220> FEATURE:
<221> NAME/KEY: CDS
<222> LOCATION: (1)..(390)
<223> OTHER INFORMATION:
<221> NAME/KEY: mat_peptide
<222> LOCATION: (67)..()
<223> OTHER INFORMATION:

<400> SEQUENCE: 9

```
atg cag caa gca ggg ctc aca ctc atg gct gtg gct gtg tgt gtg gct        48
Met Gln Gln Ala Gly Leu Thr Leu Met Ala Val Ala Val Cys Val Ala
        -20                 -15                 -10 ttt caa acc tca gaa gcc ata ctt ccc atg gcc tcc agc tgt tgc act        96
Phe Gln Thr Ser Glu Ala Ile Leu Pro Met Ala Ser Ser Cys Cys Thr
    -5              -1  1               5                   10
```

```
gag gtg tct cat cat gtt tcc gga aga ctt ctg gaa aga gtg agt tca      144
Glu Val Ser His His Val Ser Gly Arg Leu Leu Glu Arg Val Ser Ser
             15                  20                  25 tgc agc atc cag aga gct gac ggg gac tgc gac ctg gct gct gtc atc      192
Cys Ser Ile Gln Arg Ala Asp Gly Asp Cys Asp Leu Ala Ala Val Ile
         30                  35                  40 ctt cat gtt aaa cgt aga aga atc tgc atc agc ccg cac aat cgt act      240
Leu His Val Lys Arg Arg Arg Ile Cys Ile Ser Pro His Asn Arg Thr
     45                  50                  55 ttg aag cag tgg atg aga gcc tca gag gta aag aag aat ggc aga gaa      288
Leu Lys Gln Trp Met Arg Ala Ser Glu Val Lys Lys Asn Gly Arg Glu
 60                  65                  70 aac gtc tgt tct ggg aaa aaa caa ccc agc agg aag gac aga aaa ggg      336
Asn Val Cys Ser Gly Lys Lys Gln Pro Ser Arg Lys Asp Arg Lys Gly
75                  80                  85                  90 cac act acg aga aag cac aga aca cgt gga aca cac agg cac gaa gcc      384
His Thr Thr Arg Lys His Arg Thr Arg Gly Thr His Arg His Glu Ala
                 95                 100                 105 tct cgt tag                                                          393
Ser Arg
```

<210> SEQ ID NO 10
<211> LENGTH: 130
<212> TYPE: PRT
<213> ORGANISM: Mus musculus

<400> SEQUENCE: 10

```
Met Gln Gln Ala Gly Leu Thr Leu Met Ala Val Ala Val Cys Val Ala
        -20                 -15                 -10

Phe Gln Thr Ser Glu Ala Ile Leu Pro Met Ala Ser Ser Cys Cys Thr
     -5                  -1  1                   5                  10

Glu Val Ser His His Val Ser Gly Arg Leu Leu Glu Arg Val Ser Ser
             15                  20                  25

Cys Ser Ile Gln Arg Ala Asp Gly Asp Cys Asp Leu Ala Ala Val Ile
         30                  35                  40

Leu His Val Lys Arg Arg Arg Ile Cys Ile Ser Pro His Asn Arg Thr
     45                  50                  55

Leu Lys Gln Trp Met Arg Ala Ser Glu Val Lys Lys Asn Gly Arg Glu
 60                  65                  70

Asn Val Cys Ser Gly Lys Lys Gln Pro Ser Arg Lys Asp Arg Lys Gly
75                  80                  85                  90

His Thr Thr Arg Lys His Arg Thr Arg Gly Thr His Arg His Glu Ala
                 95                 100                 105

Ser Arg
```

<210> SEQ ID NO 11
<211> LENGTH: 362
<212> TYPE: DNA
<213> ORGANISM: Homo sapiens
<220> FEATURE:
<221> NAME/KEY: CDS
<222> LOCATION: (1)..(336)
<223> OTHER INFORMATION:
<221> NAME/KEY: mat_peptide
<222> LOCATION: (73)..()
<223> OTHER INFORMATION:

<400> SEQUENCE: 11

```
atg aag ggg ccc cca acc ttc tgc agc ctc ctg ctg ctg tca ttg ctc       48
Met Lys Gly Pro Pro Thr Phe Cys Ser Leu Leu Leu Leu Ser Leu Leu
        -20                 -15                 -10
```

```
ctg agc cca gac cct aca gca gca ttc cta ctg cca ccc agc act gcc      96
Leu Ser Pro Asp Pro Thr Ala Ala Phe Leu Leu Pro Pro Ser Thr Ala
         -5              -1   1               5 tgc tgt act cag ctc tac cga aag cca ctc tca gac aag cta ctg agg     144
Cys Cys Thr Gln Leu Tyr Arg Lys Pro Leu Ser Asp Lys Leu Leu Arg
 10                  15                  20 aag gtc atc cag gtg gaa ctg cag gag gct gac ggg gac tgt cac ctc     192
Lys Val Ile Gln Val Glu Leu Gln Glu Ala Asp Gly Asp Cys His Leu
 25                  30                  35                  40 cag gct ttc gtg ctt cac ctg gct caa cgc agc atc tgc atc cac ccc     240
Gln Ala Phe Val Leu His Leu Ala Gln Arg Ser Ile Cys Ile His Pro
                 45                  50                  55 cag aac ccc agc ctg tca cag tgg ttt gag cac caa gag aga aag ctc     288
Gln Asn Pro Ser Leu Ser Gln Trp Phe Glu His Gln Glu Arg Lys Leu
             60                  65                  70 cat ggg act ctg ccc aag ctg aat ttt ggg atg cta agg aaa atg ggc     336
His Gly Thr Leu Pro Lys Leu Asn Phe Gly Met Leu Arg Lys Met Gly
         75                  80                  85 tgaagcccca atagccaaat aataaa                                         362

<210> SEQ ID NO 12
<211> LENGTH: 112
<212> TYPE: PRT
<213> ORGANISM: Homo sapiens

<400> SEQUENCE: 12

Met Lys Gly Pro Pro Thr Phe Cys Ser Leu Leu Leu Ser Leu Leu
                -20                 -15                 -10

Leu Ser Pro Asp Pro Thr Ala Ala Phe Leu Leu Pro Pro Ser Thr Ala
         -5              -1   1               5

Cys Cys Thr Gln Leu Tyr Arg Lys Pro Leu Ser Asp Lys Leu Leu Arg
 10                  15                  20

Lys Val Ile Gln Val Glu Leu Gln Glu Ala Asp Gly Asp Cys His Leu
 25                  30                  35                  40

Gln Ala Phe Val Leu His Leu Ala Gln Arg Ser Ile Cys Ile His Pro
                 45                  50                  55

Gln Asn Pro Ser Leu Ser Gln Trp Phe Glu His Gln Glu Arg Lys Leu
             60                  65                  70

His Gly Thr Leu Pro Lys Leu Asn Phe Gly Met Leu Arg Lys Met Gly
         75                  80                  85

<210> SEQ ID NO 13
<211> LENGTH: 433
<212> TYPE: DNA
<213> ORGANISM: Mus musculus
<220> FEATURE:
<221> NAME/KEY: CDS
<222> LOCATION: (23)..(382)
<223> OTHER INFORMATION:
<221> NAME/KEY: mat_peptide
<222> LOCATION: (98)..()
<223> OTHER INFORMATION:

<400> SEQUENCE: 13
gaaacctcta ggctgagtga gc atg atg gag ggg ctc tcc ccc gcc agc agc     52
                         Met Met Glu Gly Leu Ser Pro Ala Ser Ser
                         -25                 -20 ctc ccg ctg tta ctg ttg ctt ctg agc ccg gct cct gaa gca gcc ttg     100
Leu Pro Leu Leu Leu Leu Leu Leu Ser Pro Ala Pro Glu Ala Ala Leu
```

```
        -15                 -10                  -5              -1   1
cct ctg ccc tcc agc act agc tgc tgt act cag ctc tat aga cag cca         148
Pro Leu Pro Ser Ser Thr Ser Cys Cys Thr Gln Leu Tyr Arg Gln Pro
             5                       10                      15 ctc cca agc agg ctg ctg agg agg att gtc cac atg gaa ctg cag gag         196
Leu Pro Ser Arg Leu Leu Arg Arg Ile Val His Met Glu Leu Gln Glu
         20                      25                      30 gcc gat ggg gac tgt cac ctc cag gct gtc gtg ctt cac ctg gct cgg         244
Ala Asp Gly Asp Cys His Leu Gln Ala Val Val Leu His Leu Ala Arg
     35                      40                      45 cgc agt gtc tgt gtt cat ccc cag aac cgc agc ctg gct cgg tgg tta         292
Arg Ser Val Cys Val His Pro Gln Asn Arg Ser Leu Ala Arg Trp Leu
 50                      55                      60                  65 gaa cgc caa ggg aaa agg ctc caa ggg act gta ccc agt tta aat ctg         340
Glu Arg Gln Gly Lys Arg Leu Gln Gly Thr Val Pro Ser Leu Asn Leu
                 70                      75                      80 gta cta caa aag aaa atg tac tca aac ccc caa cag caa aac                 382
Val Leu Gln Lys Lys Met Tyr Ser Asn Pro Gln Gln Gln Asn
             85                      90                      95 taataaagca acattagacg acaaaaaaaa aaaaaaaaa aaaaaaaaaa a                  433

<210> SEQ ID NO 14
<211> LENGTH: 120
<212> TYPE: PRT
<213> ORGANISM: Mus musculus

<400> SEQUENCE: 14

Met Met Glu Gly Leu Ser Pro Ala Ser Ser Leu Pro Leu Leu Leu
-25                 -20                 -15                 -10

Leu Leu Ser Pro Ala Pro Glu Ala Ala Leu Pro Leu Pro Ser Ser Thr
             -5              -1   1                  5

Ser Cys Cys Thr Gln Leu Tyr Arg Gln Pro Leu Pro Ser Arg Leu Leu
             10                  15                  20

Arg Arg Ile Val His Met Glu Leu Gln Glu Ala Asp Gly Asp Cys His
         25                  30                  35

Leu Gln Ala Val Val Leu His Leu Ala Arg Arg Ser Val Cys Val His
 40                  45                  50                      55

Pro Gln Asn Arg Ser Leu Ala Arg Trp Leu Glu Arg Gln Gly Lys Arg
                 60                  65                  70

Leu Gln Gly Thr Val Pro Ser Leu Asn Leu Val Leu Gln Lys Lys Met
             75                  80                  85

Tyr Ser Asn Pro Gln Gln Gln Asn
             90                  95

<210> SEQ ID NO 15
<211> LENGTH: 32
<212> TYPE: DNA
<213> ORGANISM: Homo sapiens

<400> SEQUENCE: 15
atctggcacc acaccttcta caatgagctg cg                                      32

<210> SEQ ID NO 16
<211> LENGTH: 32
<212> TYPE: DNA
<213> ORGANISM: Homo sapiens

<400> SEQUENCE: 16
cgtcatactc ctgcttgctg atccacatct gc                                      32
```

METHOD OF IMPAIRING MOVEMENT OF A CLA + MEMEORY T-CELL WITHIN OR TO THE SKIN OF A MAMMAL BY ADMINISTERING A CTACK ANTAGONIST

The present filing is continuation-in-part of U.S. Ser. No. 09/471,549, filed Dec. 23, 1999, now abandoned which is a conversion to a U.S. Utility Patent Application of provisional U.S. patent applications U.S. Ser. No. 60/113,858, filed Dec. 24, 1998, and U.S. Ser. No. 60/136,570, filed May 27, 1999, each of which is incorporated herein by reference.

FIELD OF THE INVENTION

The present invention relates to compositions related to proteins which function in controlling physiology, development, and/or differentiation of mammalian cells. In particular, it provides proteins which are implicated in the regulation of physiology, development, differentiation, or function of various cell types, e.g., chemokines, 7 transmembrane receptors, reagents related to each, e.g., antibodies or nucleic acids encoding them, and uses thereof. It also provides methods of using various chemokine compositions, and compositions used for such, and more particularly, to methods of treating skin diseases or conditions associated with misregulation of the chemokines CTACK and/or CTACK.

BACKGROUND

The immune system consists of a wide range of distinct cell types, each with important roles to play. See Paul (ed. 1997) *Fundamental Immunology* 4th ed., Raven Press, New York. The lymphocytes occupy central stage because they are the cells that determine the specificity of immunity, and it is their response that orchestrates the effector limbs of the immune system. Two broad classes of lymphocytes are recognized: the B lymphocytes, which are precursors of antibody secreting cells, and the T (thymus-dependent) lymphocytes. T lymphocytes express important regulatory functions, such as the ability to help or inhibit the development of specific types of immune response, including antibody production and increased microbicidal activity of macrophages. Other T lymphocytes are involved in direct effector functions, such as the lysis of virus infected-cells or certain neoplastic cells.

The chemokines are a large and diverse superfamily of proteins. The superfamily is subdivided into two classical branches, based upon whether the first two cysteines in the chemokine motif are adjacent (termed the "C—C" branch), or spaced by an intervening residue ("C-X-C"). A more recently identified branch of chemokines lacks two cysteines in the corresponding motif, and is represented by the chemokines known as lymphotactins. Another recently identified branch has three intervening residues between the two cysteines, e.g., CX3C chemokines. See, e.g., Schall and Bacon (1994) *Current Opinion in Immunology* 6:865–873; and Bacon and Schall (1996) *Int. Arch. Allergy & Immunol.* 109:97–109.

Many factors have been identified which influence the differentiation process of precursor cells, or regulate the physiology or migration properties of specific cell types. These observations indicate that other factors exist whose functions in immune function were heretofore unrecognized. These factors provide for biological activities whose spectra of effects may be distinct from known differentiation or activation factors. The absence of knowledge about the structural, biological, and physiological properties of the regulatory factors which regulate cell physiology in vivo prevents the modulation of the effects of such factors. Thus, medical conditions where regulation of the development or physiology of relevant cells is required remain unmanageable.

SUMMARY OF THE INVENTION

The present invention is based, in part, upon the discovery of various chemokine binding partners for 7 transmembrane receptors, and upon the surprising discovery that the CTACK and Vic chemokines are expressed on skin cells. They have been shown to have effects on immune cells related to dermatological health.

The present invention provides, e.g., methods of modulating movement of a cell within or to the skin of a mammal, the method comprising administering to the mammal an effective amount of: an antagonist of CTACK; an agonist of CTACK; an antagonist of Vic; or an agonist of Vic. Often, in the method, the modulating is blocking and the administering is an antagonist of CTACK or Vic, e.g., wherein: the movement is: within the skin, chemotactic, or chemokinetic; the administering is local, topical, systemic, subcutaneous, intradermal, or transdermal; the administering is an antagonist of CTACK or Vic; the cell is a CLA+ cell, a T cell, a dendritic cell, or a dendritic cell precursor; a dermal fibroblast; a deraml endothelial cell, or a melanocyte; or the cell moves into the dermis and/or epidermis layers of the skin. Particularly, such method will be one wherein: the antagonist is selected from a mutein of natural CTACK or Vic, an antibody which neutralizes CTACK or Vic, or an antibody which blocks GPR2 ligand binding; the mammal is subject to a transplant or skin graft; or the antagonist is administered in combination with an antibiotic, analgesic, immune suppressive therapeutic, anti-inflammatory drug, growth factor, or immune adjuvant.

In other methods, the modulating is attracting and the administering is an agonist of CTACK or Vic. In certain embodiments, the movement is: within the skin, chemotactic, or chemokinetic; the administering is local, topical, subcutaneous, intradermal, or transdermal; the administering is a CTACK or Vic ligand; the cell is a CLA+ cell, a T cell, a dendritic cell, or a dendritic cell precursor; a dermal fibroblast, a dermal endothelial cell, or a melanocyte; or the cell moves into the dermis and/or epidermis layers of the skin. Certain preferred methods will be where the agonist is selected from CTACK or Vic, or a GPR2 ligand; the mammal is subject to a cutaneous lesion; or the agonist is administered in combination with an antibiotic, analgesic, immune suppressive therapeutic, anti-inflammatory drug, growth factor, or immune adjuvant. The agonist is also administered as a cutaneous adjuvant alone.

Other aspects of the invention include methods of purifying a population of cells, the method comprising contacting the cells with CTACK or Vic, thereby resulting in the identification of cells expressing a receptor for the CTACK or Vic. Particular forms include wherein the contacting results in specific movement of the cells to a site for purification, e.g., through pores of a membrane.

The invention also provides methods of producing a ligand:receptor complex, comprising contacting: a mammalian CTACK with a GPR2 receptor; or a mammalian Vic with a GPR2 receptor; wherein at least one of the ligand or receptor is recombinant or purified, thereby allowing the complex to form. In such methods are included those wherein: the complex results in a Ca++ flux; the GPR2 receptor is on a cell; the complex formation results in a physiological change in the cell expressing the GPR2 receptor; the contacting is in combination with IL-2 and/or interferon-α; or the contacting allows quantitative detection of the ligand.

Additionally, the invention teaches methods of modulating physiology or development of a GPR2 expressing cell comprising contacting the cell to an agonist or antagonist of a mammalian Vic or CTACK, wherein one of the GPR2 receptor or the agonist or antagonist is recombinant or purified. This will include where: the antagonist is: an antibody which: neutralizes the mammalian Vic, neutralizes the mammalian CTACK, or blocks ligand binding by GPR2; or a mutein of the Vic or CTACK; or the physiology is selected from: a cellular calcium flux; a chemoattractant response; a cellular morphology modification response; phosphoinositide lipid turnover; or an antiviral response. Within such methods are where: the antagonist is an antibody and the physiology is a chemoattractant response; or the modulating is blocking, and the physiology is an inflammatory response.

Testing methods are provided, e.g., testing a compound for ability to affect GPR2 receptor-ligand interaction, the method comprising comparing the interaction of GPR2 with Vic or CTACK in the presence and absence of the compound. Among such methods are those wherein the compound is an antibody against GPR2, Vic, or CTACK.

Various GPR2 compositions are also provided, e.g., a primate GPR2, comprising sequence of MGTEVLEQ (see SEQ ID NO: 2); a nucleic acid encoding the GPR2; or an antibody which binds selectively to MGTEVLEQ (see SEQ ID NO: 2).

Also provided is a method of treating a patient suffering from a skin disorder comprising administering an effective amount of an antagonist against GPR2, Vic, or CTACK. The method further provides an antagonist which is an antibody.

DETAILED DESCRIPTION OF THE PREFERRED EMBODIMENTS

I. General

The present invention is based, in part, on the surprising discovery that the chemokines CTACK and Vic have roles in skin immunity. The skin consists of a surface layer of epithelium called the epidermis and an underlying layer of connective tissue called the dermis. Under the dermis is a layer which contains large amounts of adipose tissue, the hypodermis. The skin serves a variety of functions, and variations in the character of the dermis and epidermis occur according to functional demands. The appendages of the skin, hair, nails, and sweat and sebaceous glands, are such local specializations of the epidermis. Together, the skin and its appendages form the integument. See, e.g., Fitzpatrick, et al. (eds. 1993) *Dermatology in General Medicine* 4th ed., McGraw-Hill, NY; Bos (ed. 1989) *Skin Immune System* CRC Press, Boca Raton, Fla.; Callen (1996) *General Practice Dermatology* Appleton and Lange; Rook, et al. (eds. 1998) *Textbook of Dermatology* Blackwell; Habifor and Habie (1995) *Clinical Dermatology: A Color Guide to Diagnosis and Therapy* Mosby; and Grob (ed. 1997) *Epidemiology, Causes and Prevention of Skin Diseases* Blackwell.

The epidermis consists of many different cell types in various proportions. The most prevalent cell type is keratinocytes, which make up some 95% of the cells. Cells in the 1–2% range include melanocytes and Langerhans cells. The Langerhans cells are particularly important because they trap antigens that have penetrated the skin, and transport antigens to regional lymph nodes. A small population of γδT cells can also reside in the epidermis.

The dermis varies in thickness in different regions of the body. It is tough, flexible, and highly elastic, and consists of a network of collagen fibers with abundant elastic fibers. The connective tissue is arranged into deep reticular and superficial papillary layers.

In addition, the invention provides chemokine-receptor matchings of chemokines with a 7 transmembrane receptor. See, e.g., Ruffolo and Hollinger (eds. 1995) *G-Protein Coupled Transmembrane Signaling Mechanisms* CRC Press, Boca Raton, Fla.; Watson and Arkinstall (1994) *The G-Protein Linked Receptor FactsBook* Academic Press, San Diego, Calif.; Peroutka (ed. 1994) *G Protein-Coupled Receptors* CRC Press, Boca Raton, Fla.; Houslay and Milligan (1990) *G-Proteins as Mediators of Cellular Signaling Processes* Wiley and Sons, New York, N.Y. Human and mouse embodiments are described herein.

Among the many types of ligands which mediate biology via 7 transmembrane receptors are chemokines and certain proteases. Chemokines play an important role in immune and inflammatory responses by inducing migration and adhesion of leukocytes. See, e.g., Schall (1991) *Cytokine* 3:165–183; and Thomson (ed.) *The Cytokine Handbook* Academic Press, NY. Chemokines are secreted by activated leukocytes and act as chemoattractants for a variety of cells which are involved in inflammation. Besides chemoattractant properties, chemokines have been shown to induce other biological responses, e.g., modulation of second messenger levels such as $Ca^{++}$; inositol phosphate pool changes (see, e.g., Berridge (1993) *Nature* 361:315–325 or Billah and Anthes (1990) *Biochem. J.* 269:281–291); cellular morphology modification responses; phosphoinositide lipid turnover; possible antiviral responses; and others. Thus, the chemokines provided herein may, alone or in combination with other therapeutic reagents, have advantageous combination effects.

Moreover, there are reasons to suggest that chemokines may have effects on other cell types, e.g., attraction or activation of monocytes, dendritic cells, T cells, eosinophils, basophils, and/or neutrophils. They may also have chemoattractive effects on various neural cells including, e.g., dorsal root ganglia neurons in the peripheral nervous system and/or central nervous system neurons.

G-protein coupled receptors, e.g., chemokine receptors, are important in the signal transduction mechanisms mediated by their ligands. They are useful markers for distinguishing cell populations, and have been implicated as specific receptors for retroviral infections.

The chemokine superfamily was classically divided into two groups exhibiting characteristic structural motifs, the Cys-X-Cys (C-X-C) and Cys-Cys (C—C) families. These were distinguished on the basis of a single amino acid insertion between the NH-proximal pair of cysteine residues and sequence similarity. Typically, the C-X-C chemokines, i.e., IL-8 and MGSA/Gro-α act on neutrophils but not on monocytes, whereas the C—C chemokines, i.e., MIP-1α and RANTES, are potent chemoattractants for monocytes and lymphocytes but not neutrophils. The CC chemokines are preferentially effective on macrophages, lymphocytes, and eosinophils. See, e.g., Miller, et al. (1992) *Crit. Rev. Immunol.* 12:17–46. A recently isolated chemokine, lymphotactin, does not belong to either group and may constitute a first member of a third chemokine family, the C family. Lymphotactin does not have a characteristic CC or CXC motif, and acts on lymphocytes but not neutrophils and monocytes. See, e.g., Kelner et al. (1994) *Science* 266:1395–1399. This chemokine defines a new C chemokine family. Even more recently, another chemokine exhibiting a CX3C motif has been identified, which establishes a fourth structural class.

The chemokine GWCC, from mouse and human, has been described earlier in WO 98/23750, which is incorporated herein by reference for all purposes. Based upon new observations directed to the biology of this chemokine, it is herein referred to as cutaneous-T-cell-attracting chemokine or CTACK. The sequences are provided in SEQ ID NO: 11–14, and have been deposited in the GenBank/EMBL/DDBJ databases under the accession numbers AF082392 (mouse CTACK) and AF082393 (human CTACK). The human and mouse CTACK clones map to syntenic chromosomal regions, human segment 9p13 and the proximal region of mouse chromosome 4, respectively. Other C—C chemokines, e.g., 6Ckine and MIP-3β, also map to these chromosomal regions. Likewise, the chemokine Vic is described. See SEQ ID NO: 5–10. The Vic chemokine exhibits similar biology to CTACK, but is slightly different, e.g., in Peyer's Patch as well as mammary gland, salivary gland, and small intestine expression, epithelial surfaces with the topological exterior. Vic also has a more regulated expression pattern, e.g., upregulation in psoriasis, than CTACK.

The described chemokines or receptors should be important for mediating various aspects of cellular, organ, tissue, or organismal physiology or development. In particular, the Vic chemokine is a classic pro-inflammatory chemokine, which mediates inflammatory processes. The CTACK is a cutaneously expressed chemokine. See, e.g., U.S. Ser. No. 08/978,964 (now abandoned) and related cases.

In contrast to naive lymphocytes, memory/effector lymphocytes can access non-lymphoid effector sites and display restricted, often tissue-selective, migration behavior. The cutaneous lymphocyte-associated antigen (CLA) defines a well described subset of circulating memory T cells that selectively localize in cutaneous sites mediated in part by the interaction of CLA with its vascular ligand E-selectin. Picker. et al. (1991) *Nature* 349:796–799; and Rossiter, et al. (1994) *Eur. J. Immunol.* 24:205–210. E-selectin is broadly expressed in inflamed endothelium; thus, specific infiltration of skin by CLA cells must require additional cues. Herein is description of particular C—C chemokines, one originally designated GWCC but herein referred to as CTACK, and the other Vic. See U.S. Ser. No. 08/978.964 (now abandoned) or WO 98/23750, which are incorporated herein by reference for all purposes.

Based upon the new information directed to function, one chemokine is herein referred to as cutaneous-T-cell-attracting chemokine or CTACK. Both human and mouse CTACK are detected exclusively in skin, specifically in the mouse epidermis and in human keratinocytes. CTACK message is upregulated in keratinocytes upon treatment with pro-inflammatory cytokines. CTACK selectively attracts CLA$^+$ memory T cells, and also had effects on skin dendritic cells (Langerhans cells) and their precursors. The chemokine Vic has similar characteristics, but is also expressed in the gut and is sometimes upregulated. These features suggest an important role for CTACK and/or Vic in recruitment of CLA$^+$ T cells and dendritic cells to cutaneous sites. CTACK is the first chemokine described that is specifically expressed in the skin and that selectively attracts a tissue-specific subpopulation of memory lymphocytes.

Having identified the CTACK and Vic as skin related chemokines, they will find use in affecting medical abnormalities of the skin. Common skin disorders involving the immune system include psoriasis, skin cancers, carcinomas, inflammation, allergies, contact and allergic dermatitis, wound healing, infections (including microbial, viral, and parasitic), and many others. See, e.g., *The Merck Manual*, particularly the chapter on dermatologic disorders. These therapeutics may have useful effects on growth or health of appendages of the skin, including, e.g., hair, nails, and sweat and sebaceous glands.

Psoriasis is a chronic inflammatory skin disorder that is associated with hyperplastic epidermal keratinocytes and infiltrating mononuclear cells, including CD4+ memory T cells, neutrophils and macrophages. Because of this highly mixed inflammatory picture and the resulting complex interrelationships between these different cells, it has been very difficult to dissect the mechanisms that underlie the induction and progression of the disease.

This hypothesis also implies that although dormant autoreactive T cells may pre-exist in susceptible individuals, an environmental stimulus is necessary to trigger disease induction. Others believe that the immune system plays only a minor modulatory role in the disease process and that hyperproliferation of keratinocytes is, in fact, the initiating event in a genetically susceptible host. Research into the pathogenesis of psoriasis has long been hindered by the lack of suitable animal models.

There is growing data indicating that T cells and not keratinocytes are the primary pathogenic component in the disease. The observations herein provide evidence to support the concept that psoriasis-like conditions can indeed result from unregulated T cell responses.

Also, skin cancers such as basal cell and squamous cell carcinoma are among the most common malignancies. See, e.g., Miller and Maloney (eds. 1997) *Cutaneous Oncology: Pathophysiology, Diagnosis, and Management* Blackwell; Emmett and Orourke (1991) *Malignant Skin Tumours* Churchill Livingstone; Friedman (1990) *Cancer of the Skin* Saunders. Most of those tumors arise in sun exposed areas of the skin. Immune regulation or clearance of such tumors may depend upon function of the skin immune system. Cells which effect such may be compromised by local misregulation or suppression. The CTACK or Vic or antagonists may break a temporary homeostasis which suppresses normal immune response, thereby leading to activation of proper regulatory and immune pathways.

Contact or allergic dermatitis is a superficial inflammation of the skin, characterized by vesicles (when acute), redness, edema, oozing, crusting, scaling, and itching. See, e.g., Lepoittevin (ed. 1998) *Allergic Contact Dermatitis: The Molecular Basis* Springer-Verlag; Rietschel and Fowler (eds. 1995) *Fisher's Contact Dermatitis* Lippincott; and Rycroft, et al. (eds. 1994) *Textbook of Contact Dermatitis* Springer-Verlag. The term eczematous dermatitis is often used to refer to a vesicular dermatitis. Dermatitis may accompany various immune deficiency conditions or diseases, inborn metabolic disorders, or nutritional deficiency diseases. Certain of the symptoms of such conditions may be treated using the present invention.

Pruritus is a sensation that the patient attempts to relieve by scratching. See, e.g., Fleischer and Fleischer (1998) *The Clinical Management of Itching: Therapeutic Protocols for Pruritus* Parthenon. Many parasitic or infectious conditions may result in those symptoms, which conditions may be cleared by proper reactivation or suppression of immune functions in the skin. Likewise with various allergic or other immune reactions to exposure to various allergic or inflammatory antigens.

Vic and CTACK bind and signal thorough the common receptor GPR-2 as demonstrated by their ability to induce chemotaxis in cells transfected with GPR-2 cDNA but not untransfected cells or cells transfected with truncated GPR-2 (missing the 8 N-terminal amino acids). Vic, unlike CTACK, also binds CCR3, which is a receptor expressed on eosinophils. These chemokines share a receptor on CLA+ T cells, as demonstrated by the finding that they are able to desensitize each other's chemotactic response.

Both Vic and CTACK selectively chemoattract CLA+ skin-homing memory T cells and not other memory T cell subsets including β7+ gut homing T cells. Neither CTACK nor Vic attract naive T cells, B cells or monocytes.

Similar to other chemokines, CTACK immobilizes on the extracellular matrix and the surface of endothelial cells. CTACK thus may play a role in several steps of the lymphocyte homing process since endothelial cell-bound CTACK may serve as a counterligand to mediate firm adhesion and initiate transendothelial migration. In addition, immobilization of CTACK on dermal extracellular matrix and fibroblasts may sustain a chemokine gradient directing skin-infiltrating lymphocytes from perivascular pockets to subepidermal locations.

In vitro, TNF-α/IL-1β upregulates mouse and human CTACK production and conversely, glucocorticosteroids down-regulate this chemokine in vivo. Results of recent clinical trials investigating the efficacy of a neutralizing anti-human TNF-α antibody clearly show the dominant role of this proinflammatory cytokine in the pathogenesis of inflammatory and autoimmune diseases including rheumatoid arthritis, Crohn's disease and psoriasis (see, e.g., Bondeson and Maini (2001) *Int. J. Clin. Prac,* 55:211–216 and Kirby, et al. (2001) *Clin. Exp. Dermatol.* 26:27–29). Moreover, the regulation of CTACK by glucocorticosteroids in vivo indicates that this novel CC chemokine may be directly or indirectly regulated by NFκB and IκB and underscores the potential therapeutic relevance for the inhibition of CTACK and CCR10.

In vivo proof-of-principle studies showed that neutralization of CTACK/CCR10 interactions impairs lymphocyte recruitment to the skin leading to suppressed allergen-induced skin inflammation. Moreover, direct comparisons indicated that neutralization of CTACK was superior to the topical immunosuppressant FK506/tacrolimus in inhibiting antigen-specific skin inflammation.

Taken together a model emerges in which CTACK/CCR10 interaction is involved in several steps along the recruitment pathway of skin-homing T cells under homeostatic and inflammatory conditions. During inflammation, CTACK displayed on endothelial cells of the superficial dermal plexus may cooperate with inflammatory chemokines such as CCL17/TARC, CCL20/MIP-3α, CXCL9/Mig and CXCL10/IP-10 to mediate firm adhesion of lymphocytes and initiate transendothelial migration (see, e.g., Cinamon, et al. (2001) *Nat. Immunol.* 2:515–522; Baekkevold, et al. (2001) *J. Exp. Med.* 193: 1105–1112; Grabovsky, et al. (2000) *J. Exp. Med.* 192:495–506; Butcher and Picker (1996) *Science* 272:60–66; Campbell, et al. (1999) *Nature* 400:776:780; Andrew, et al. (2001) *J. Immunol.* 166:103–111; Campbell, et al. (1998) *Science* 279:381–384; and Piali, et al. (1998) *J. Immunol.* 28:961–972.

CTACK/CCR10 interactions may play an important role in both skin homeostasis and the initiation of skin inflammation. CTACK represents a skin-associated homeostatic chemokine which is upregulated upon inflammation. In addition, CTACK/CCR10 interaction is important for lymphocyte recruitment to the skin and the elicitation of antigen-specific skin inflammation in vivo and, therefore, may represent a promising target for the development of novel and selective therapeutics for inflammatory or autoimmune skin diseases.

II. Purified Chemokines; Receptors

Nucleotide and derived amino acid sequences of a primate chemokine receptor, e.g., from human, and from rodent, e.g., from mouse, designated GPR2 are shown in SEQ ID NOs: 1, 2, 3, and 4. The genes encode novel proteins exhibiting structure and motifs characteristic of a chemokine receptor. See Marchese, et al. (1994) *Genomics* 23:609–618. GPR-2 mRNA is expressed in CLA+ T cells but not other memory T cell subsets or naive T cells; thus, since CLA+ T cells are known to play a key role in cutaneous inflammation, any method for blocking GPR2 interaction with CTACK or Vic is a potentially important therapeutic agent.

Nucleotide and derived amino acid sequences of the two chemokines Vic and CTACK are provided in SEQ ID NOs: 5–14. The present invention has matched the human GPR2 chemokine receptor with chemokines Vic and CTACK.

Certain general descriptions of physical properties of polypeptides, nucleic acids, and antibodies, where directed to one embodiment clearly are usually applicable to other chemokines or receptors described herein.

These amino acid sequences, provided amino to carboxy, are important in providing sequence information on the chemokine ligand or receptor, allowing for distinguishing the protein from other proteins, particularly naturally occurring versions. Moreover, the sequences allow preparation of peptides to generate antibodies to recognize and distinguish such segments, and allow preparation of oligonucleotide probes, both of which are strategies for isolation, e.g., cloning, of genes encoding such sequences, or related sequences, e.g., natural polymorphic or other variants, including fusion proteins. Similarities of the chemokines have been observed with other cytokines. See, e.g., Bosenberg, et al. (1992) *Cell* 71:1157–1165; Huang, et. al. (1992) *Molecular Biology of the Cell* 3:349–362; and Pandiella, et al. (1992) *J. Biol. Chem.* 267:24028–24033. Likewise for the GPC receptors.

As used herein, the term "GPR2" shall encompass, when used in a protein context, a protein having mature amino acid sequence, as shown in SEQ ID NO: 2 or 4. The invention also embraces selective polypeptides, e.g., comprising a specific fragment of such protein. The invention also encompasses a polypeptide which is a primate species counterpart, e.g., which exhibits similar sequence, and is more homologous in natural encoding sequence than other genes from a primate species. Typically, such chemokine receptor will also interact with its specific binding components, e.g., ligand, or antibodies which bind to it. These binding components, e.g., antibodies, typically bind to the chemokine receptor with high affinity, e.g., at least about 100 nM, usually better than about 30 nM, preferably better than about 10 nM, and more preferably at better than about 3 nM. Similarly applicable terms apply to the chemokine ligands.

The term "polypeptide" as used herein includes a significant fragment or segment, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids, e.g., about 35, 40, 45, 50, 60, 75, 80, 100, 120, etc. Similar proteins will likely comprise a plurality of such segments. Such fragments may have ends which begin and/or end at virtually all positions, e.g., beginning at residues 1, 2, 3, etc., and ending at, e.g., 69, 68, 67, 66, etc., in all combinatorial pairs in the coding segment. Particularly interesting peptides have ends corresponding to structural domain boundaries, e.g., intracellular or extracellular loops of the receptor embodiments. Such peptides will typically be immunogenic peptides, or may be concatenated to generate larger polypeptides. Short peptides may be attached or coupled to a larger carrier.

The term "binding composition" refers to molecules that bind with specificity to the respective chemokine or receptor, e.g., in a ligand-receptor type fashion or an antibody-antigen interaction. These compositions may be compounds, e.g., proteins, which specifically associate with the chemokine or receptor, including natural physiologically relevant protein-protein interactions, either covalent or non-covalent. The binding composition may be a polymer, or another chemical reagent. No implication as to whether the chemokine presents a concave or convex shape in its ligand-receptor interaction is necessarily represented, other than the interaction exhibit similar specificity, e.g., specific affinity. A functional analog may be a ligand with structural modifications, or may be a wholly unrelated molecule, e.g., which has a molecular shape which interacts with the appropriate ligand binding determinants. The ligands may serve as agonists or antagonists of a physiological or natural receptor, see, e.g., Goodman, et al. (eds. 1990) *Goodman & Gilman's: The Pharmacological Bases of Therapeutics* (8th ed.), Pergamon Press. The term expressly includes antibodies, polyclonal or monoclonal, which specifically bind to the respective antigen.

Substantially pure means that the protein is free from other contaminating proteins, nucleic acids, and/or other biologicals typically derived from the original source organism. Purity may be assayed by standard methods, and will ordinarily be at least about 40% pure, more ordinarily at least about 50% pure, generally at least about 60% pure, more generally at least about 70% pure, often at least about 75% pure, more often at least about 80% pure, typically at least about 85% pure, more typically at least about 90% pure, preferably at least about 95% pure, more preferably at least about 98% pure, and in most preferred embodiments, at least 99% pure. Analyses will typically be by weight, but may be by molar amounts.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 40° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified, e.g., to conform to standard buffers used in physiological or analytical contexts.

The size and structure of the polypeptide should generally be in a substantially stable state, and usually not in a denatured state, though in certain circumstances denatured protein will be important. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically at least about 5, preferably at least 6, and typically less than 10, preferably less than 9, and more preferably about 7.5. On some occasions, a detergent will be added, typically a mild non-denaturing one, e.g., CHS (cholesteryl hemisuccinate) or CHAPS (3-([3-cholamido-propyl]dimethylammonio)-1-propane sulfonate), or a low enough concentration as to avoid significant disruption of structural or physiological properties of the protein.

Solubility is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W.H. Freeman; and Cantor and Schimmel (1980) *Biophysical Chemistry*, parts 1–3, W.H. Freeman & Co., San Francisco. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S.

III. Physical Variants

This invention also encompasses proteins or peptides having substantial amino acid sequence homology with the amino acid sequence of each respective receptor. The variants include species or polymorphic variants.

Amino acid sequence homology, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic and interspecies variations in each respective protein sequence. Typical homologous proteins or peptides will have from 25–100% homology (if gaps can be introduced), to 50–100% homology (if conservative substitutions are included) with the amino acid sequence of the appropriate chemokine or receptor. Homology measures will be at least about 35%, generally at least 40%, more generally at least 45%, often at least 50%, more often at least 55%, typically at least 60%, more typically at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443–453; Sankoff, et al. (1983) Chapter One in *Time Warps, String Edits, and Macromolecules: The Theory and Practice of Sequence Comparison* Addison-Wesley, Reading, Mass.; and software packages from IntelliGenetics, Mountain View, Calif.; and the University of Wisconsin Genetics Computer Group, Madison, Wis.

Each of the isolated chemokine or GPC receptor DNAs can be readily modified by nucleotide substitutions, nucleotide deletions, nucleotide insertions, and inversions of nucleotide stretches. These modifications may result in novel DNA sequences which encode these antigens, their derivatives, or proteins having similar physiological, immunogenic, or antigenic activity. These modified sequences can be used to produce mutant antigens or to enhance expression, or to introduce convenient enzyme recognition sites into the nucleotide sequence without significantly affecting the encoded protein sequence. Enhanced expression may involve gene amplification, increased transcription, increased translation, and other mechanisms. Such mutant receptor derivatives include predetermined or site-specific mutations of the respective protein or its fragments. "Mutant chemokine" encompasses a polypeptide otherwise falling within the homology definition of the chemokine as set forth above, but having an amino acid sequence which differs from that of the chemokine as found in nature, whether by way of deletion, substitution, or insertion. Likewise for the GPCRs. These include amino acid residue substitution levels from none, one, two, three, five, seven, ten, twelve, fifteen, etc. In particular, "site specific mutant" generally includes proteins having significant homology with a protein having sequences of SEQ ID NO: 2 or 4, and as sharing various biological activities, e.g., antigenic or immunogenic, with those sequences, and in preferred embodiments contain most of the disclosed sequences, particularly those found in various groups of animals. As stated before, it is emphasized that descriptions are generally meant to encompass the various chemokine or receptor proteins from other members of related groups, not limited to the mouse or human embodiments specifically discussed.

Although site specific mutation sites are often predetermined, mutants need not be site specific. Chemokine or receptor mutagenesis can be conducted by making amino acid insertions or deletions. Substitutions, deletions, insertions, or combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also Sambrook, et al. (1989) and Ausubel, et al. (1987 and Supplements). Many structural features are known about the chemokines and GPCRs which allow determination of whether specific residues are embedded into the core of the secondary or tertiary structures, or whether the residues will have relatively little effect on protein folding. Preferred positions for mutagenesis are those which do not prevent functional folding of the resulting protein.

The mutations in the DNA normally should not place coding sequences out of reading frames and preferably will not create complementary regions that could hybridize to produce secondary mRNA structure such as loops or hairpins. But certain situations exist where such problems are compensated. See, e.g., Gesteland and Atkins (1996) *Ann. Rev. Biochem.* 65:741–768.

The present invention also provides recombinant proteins, e.g., heterologous fusion proteins using segments from these proteins, or antibodies. A heterologous fusion protein is a fusion of proteins or segments which are naturally not normally fused in the same manner. Thus, the fusion product of an immunoglobulin with a receptor polypeptide is a continuous protein molecule having sequences fused in a typical peptide linkage, typically made as a single translation product and exhibiting properties derived from each source peptide. A similar chimeric concept applies to heterologous nucleic acid sequences.

In addition, new constructs may be made from combining similar functional or structural domains from other proteins. For example, ligand-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992. Thus, new chimeric polypeptides exhibiting new combinations of specificities will result from the functional linkage of ligand-binding specificities and other functional domains. Such may be chimeric molecules with mixing or matching of the various structural segments, e.g., the -sheet or -helix structural domains for the chemokine, or receptor segments corresponding to each of the transmembrane segments (TM1–TM7), or the intracellular (cytosolic, C1–C4) or extracellular (E1–E4) loops from the various receptor types. The C3 loop is particularly important.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

IV. Functional Variants

Mammalian CTACK chemokines were described previously in U.S. Ser. No. 08/978,964 (now abandoned), which describes various migratory assays. Various agonists and antagonists of the natural ligands can be produced. The migration assays may take advantage of the movement of cells through pores in membranes. Chemotaxis may be measured thereby. Alternatively, chemokinetic assays may be developed, which measure the induction of kinetic movement, not necessarily relative to a gradient, per se.

CTACK or Vic agonists will exhibit some or all of the signaling functions of the respective chemokine, e.g., binding and chemoattracting the appropriate cells. Various mammalian CTACK or Vic sequences may be evaluated to determine what residues are conserved across species, suggesting what residues may be changed without dramatic effects on biological activity. Alternatively, conservative substitutions are likely to retain biological activity, thus leading to variant forms of the chemokine which will retain agonist activity. Standard methods for screening mutant or variant CTACK or Vic polypeptides will determine what sequences will be useful therapeutic agonists.

In addition, certain nucleic acid expression methods may be applied. For example, in skin graft contexts, it may be useful to transfect the grafts with nucleic acids which will be expressed, as appropriate. Various promoters may be operably linked to the gene, thereby allowing for regulated expression.

Alternatively, antagonist activity may be tested for. Tests for ability to antagonize chemoaftractant activity can be developed using assays as described below. Various ligand homologs can be created which retain receptor binding capacity, but lacking signaling capability can be prepared. Small molecules may also be screened for ability to antagonize CTACK function, e.g., chemoattraction, receptor binding, Ca++ flux, and other effects mediated by CTACK. See generally Gilman, et al. (eds. 1990) *Goodman and*

Gilman's: The Pharmacological Bases of Therapeutics, 8th Ed., Pergamon Press; Remington's Pharmaceutical Sciences, 17th ed. (1990), Mack Publishing Co., Easton, Pa., each of which is incorporated herein by reference.

The blocking of physiological response to various embodiments of these chemokines or GPCRs may result from the inhibition of binding of the ligand to its receptor, likely through competitive inhibition. Thus, in vitro assays of the present invention will often use isolated protein, membranes from cells expressing a recombinant membrane associated receptor, e.g., ligand binding segments, or fragments attached to solid phase substrates. These assays will also allow for the diagnostic determination of the effects of either binding segment mutations and modifications, or ligand mutations and modifications, e.g., ligand analogs.

This invention also contemplates the use of competitive drug screening assays, e.g., where neutralizing binding compositions, e.g., antibodies, to antigen or receptor fragments compete with a test compound for binding to the protein. In this manner, the antibodies can be used to detect the presence of polypeptides which share one or more antigenic binding sites of the ligand and can also be used to occupy binding sites on the protein that might otherwise interact with a receptor.

Additionally, neutralizing antibodies against a specific chemokine embodiment and soluble fragments of the chemokine which contain a high affinity receptor binding site, can be used to inhibit chemokine activity in tissues, e.g., tissues experiencing abnormal physiology.

Screens to evaluate the binding and activity of mAbs and binding compositions encompass a variety of methods. Binding can be assayed by detectably labeling the antibody or binding composition as described above. Cells responsive to CTACK or Vic can be used to assay antibody or binding composition.

To evaluate CTACK or Vic chemoattraction or chemokinetic ability, experimental animals, e.g., mice, are preferably used. Skin, e.g., Langerhans, cell counts are made prior to and at various time points after administration of a bolus of the candidate agonist or antagonist. Levels are analyzed in various samples, e.g., blood, serum, nasal or pulmonary lavages, or tissue biopsy staining. A successful depleting mAb or binding composition will significantly lower the level of CLA+ cells. Such may be at least about 10%, preferably at least about 20%, 30%, 50%, 70%, or more.

Evaluation of antibodies can be performed in other animals, e.g., humans using various methods. For example, blood samples are withdrawn from patients suffering from a skin related disease or disorder before and after treatment with a candidate mAb.

The exquisite tissue-selective homing of lymphocytes has long been appreciated as central for the control of systemic immune responses. Recent advances in the field support a model in which leukocyte homing is achieved by sequential engagement of differentially expressed and independently regulated vascular and leukocyte adhesion molecules, and signaling receptors and their ligands. Butcher and Picker (1996) *Science* 272:60–66. The observation that chemokines, a superfamily of small secreted proteins with G protein-coupled receptors (Baggiolini (1998) *Nature* 392:565–568) can attract leukocytes led to the hypothesis that chemokines provide key signals directing recruitment of T lymphocyte subsets into lymphoid and extra-lymphoid immune effector sites. The skin-specific expression of CTACK and/or Vic coupled with its selective chemoattraction for CLA+ skin-homing memory T cells provides data supporting the hypothesis that there are tissue-specific chemokines that selectively attract functionally unique subsets of memory lymphocytes.

As such, the present invention provides means to purify desired, e.g., CLA+ cells. The chemoattractive or chemokinetic effects on those cells can be the basis of purification methods. Methods exist for selective migration and recovery of cells to or from the chemokine, e.g., through porous membrane, or to various locations in a culture. Other methods exist to selectively separate cells of particular shapes from others. Alternatively, labeling can be used to FACS sort cells which specifically bind the chemokine. Populations of substantially homogeneous Langerhans or skin derived cells will have important utility in research or therapeutic environments.

While CTACK and Vic exhibit effects on CLA+ cells, other cells which may also be responsive include fibroblasts, dermal endothelial cells, and melanocytes. Effects on various cell types may be indirect, as well as direct. A statistically significant change in the numbers of cells will typically be at least about 10%, preferably 20%, 30%, 50%, 70%, 90%, or more. Effects of greater than 100%, e.g., 130%, 150%, 2×, 3×, 5×, etc., will often be desired. The effects may be specific in causing chemotaxis to specific points, or may be chemokinetic, in inducing general movement of cells, but not necessarily in a specific direction.

CTACK can induce integrin-mediated adhesion to the vascular ligands ICAM-1 and VCAM-1. ICAM-1 or VCAM-1 are vascular adhesion molecules (adhesion molecules expressed by endothelial cells lining the vessels) and are known to be upregulated on endothelial cells in response to proinflammatory stimulation in vitro and in vivo. These adhesion molecules support leukocyte adhesion through interaction with integrin molecules (ICAM-1 binds to the $\beta 2$ integrins LFA-1 and MAC-1) and VCAM-1 binds to the $\alpha 4$ integrins $\alpha 4\beta 1$ and $\alpha 4\beta 7$. Treatment of cells with certain chemokines (but not all chemokines) can cause modulation of the integrins resulting in much better binding of the cells to these vascular ligands. CTACK can cause this modulation: treatment of T cells or a T cell line expressing GPR2 causes a rapid (2 minutes) increase in binding ability. This indicates that CTACK could be responsible for adhesion of CLA+ T cells to the endothelial cells in the skin.

CTACK can also mediate transendothelial migration of CLA+ T cells across stimulated endothelial monolayers. In these experiments, endothelial cells are grown in transwell chambers, stimulated with, for example, tumor necrosis factor-alpha (TNFα), CTACK is placed in the lower well and memory T cells are placed in the top chamber. CTACK causes the CLA+ T cells (but n ot other memory T cells including β7 T cells) to migrate across the monolayer into the lower chamber. This indicates that CTACK can mediate recruitment of T cells to cutaneous inflammatory sites by inducing migration of CLA+ T cells through the endothelial cells lining the blood vessels.

This suggests usefulness of these chemokines or antagonists in the treatment of medical conditions or diseases associated with immunological conditions of the skin. See, e.g., Bos (ed. 1990) *Skin Immune System* CRC Press, Boca Raton, Fla.; Fitzpatrick, et al. (eds. 1993) *Dermatology in General Medicine* (4th ed.) McGraw-Hill, NY; Rook, et al. (eds. 1998) *Textbook of Dermatology* Blackwell; Habifor and Habie (1995) *Clinical Dermatology: A Color Guide to Diagnosis and Therapy* Mosby; Grob (ed. 1997) *Epidemiology, Causes and Prevention of Skin Diseases* Blackwell; Frank, et al. (eds. 1995) *Samter's Immunologic Diseases,* 5th Ed., vols. I–II, Little, Brown and Co., Boston, Mass.; Coffman, et al (1989) *Science* 245:308–310; and Frick, et al. (1988) *J. Allergy Clin. Immunol.* 82:199–225.
The agonists or antagonists described may be combined with other treatments of the medical conditions described herein, e.g., an antibiotic, immune suppressive therapeutic, immune adjuvant, analgesic, anti-inflammatory drug, growth factor, cytokine, vasodilator, or vasoconstrictor.

"Derivatives" of chemokine antigens include amino acid sequence mutants, glycosylation variants, and covalent or aggregate conjugates with other chemical moieties. Covalent derivatives can be prepared by linkage of functionalities to groups which are found in chemokine amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or nucleoside or nucleotide derivatives, e.g., guanyl derivatized.

A major group of derivatives are covalent conjugates of the respective chemokine or receptor or fragments thereof with other proteins or polypeptides. These derivatives can be synthesized in recombinant culture such as N- or C-terminal fusions or by the use of agents known in the art for their usefulness in cross-linking proteins through reactive side groups. Preferred chemokine derivatization sites with cross-linking agents are at free amino groups, carbohydrate moieties, and cysteine residues.

Fusion polypeptides between these chemokines or receptors and other homologous or heterologous proteins, e.g., other chemokines or receptors, are also provided. Many growth factors and cytokines are homodimeric entities, and a repeat construct may have various advantages, including lessened susceptibility to proteolytic cleavage. Moreover, many cytokine receptors require dimerization to transduce a signal, and various dimeric ligands or domain repeats can be desirable. Homologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of a ligand, e.g., a receptor-binding segment, so that the presence or location of the fused ligand, or a binding composition, may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, a FLAG fusion, and yeast alpha mating factor. See, e.g., Godowski, et al. (1988) *Science* 241:812–816.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, guanylation, sulfonation, biotinylation, or the addition or removal of other moieties, particularly those which have molecular shapes similar to phosphate or guanyl groups. In some embodiments, the modifications will be useful labeling reagents, or serve as purification targets, e.g., affinity tags as FLAG.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (2d ed.), Vols. 1–3, Cold Spring Harbor Laboratory. Techniques for synthesis of polypeptides are described, for example, in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach*, IRL Press, Oxford; and chemical ligation, e.g., Dawson, et al. (1994) *Science* 266:776–779, a method of linking long synthetic peptides by a peptide bond.

This invention also contemplates the use of derivatives of these chemokines or receptors other than variations in amino acid sequence or glycosylation. Such derivatives may involve covalent or aggregative association with chemical moieties. These derivatives generally include: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a chemokine antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-chemokine antibodies or its receptor. These chemokines can also be labeled with a detectable group, for example radioiodinated by the chloramine T procedure, covalently bound to rare earth chelates, or conjugated to a fluorescent moiety for use in diagnostic assays. Purification of chemokine, receptor, or binding compositions may be effected by immobilized antibodies or receptor.

Other modifications may be introduced with the goal of modifying the therapeutic pharmacokinetics or pharmacodynamics of a target chemokine. For example, certain means to minimize the size of the entity may improve its pharmacoaccessibility; other means to maximize size may affect pharmacodynamics. Similarly, changes in ligand binding kinetics or equilibrium of a receptor may be engineered.

A solubilized chemokine or receptor or appropriate fragment of this invention can be used as an immunogen for the production of antisera or antibodies specific for the ligand, receptor, or fragments thereof. The purified proteins can be used to screen monoclonal antibodies or chemokine-binding fragments prepared by immunization with various forms of impure preparations containing the protein. In particular, antibody equivalents include antigen binding fragments of natural antibodies, e.g., Fv, Fab, or F(ab)$_2$. Purified chemokines can also be used as a reagent to detect antibodies generated in response to the presence of elevated levels of the protein or cell fragments containing the protein, both of which may be diagnostic of an abnormal or specific physiological or disease condition. Additionally, chemokine protein fragments, or their concatenates, may also serve as immunogens to produce binding compositions, e.g., antibodies of the present invention, as described immediately below. For example, this invention contemplates antibodies raised against certain amino acid sequences, e.g., SEQ ID NO: 2, 4, 6, 8, 10, 12, or 14, or proteins containing them. In particular, this invention contemplates antibodies having binding affinity to or being raised against specific fragments, e.g., those which are predicted to lie on the outside surfaces of protein tertiary structure. Similar concepts apply to antibodies specific for receptors of the invention.

The present invention contemplates the isolation of additional closely related species variants. Southern and Northern blot analysis should establish that similar genetic entities exist in other related mammals, and establish the stringency of hybridization conditions to isolate such. It is likely that these chemokines and receptors are widespread in species variants, e.g., among the rodents and the primates.

The invention also provides means to isolate a group of related chemokines or receptors displaying both distinctness and similarities in structure, expression, and function. Elucidation of many of the physiological effects of the proteins will be greatly accelerated by the isolation and characterization of distinct species variants of the ligands. Related genes found, e.g., in various computer databases will also be useful, in many instances, for similar purposes with structurally related proteins. In particular, the present invention provides useful probes or search features for identifying additional homologous genetic entities in different species.

The isolated genes will allow transformation of cells lacking expression of a corresponding chemokine or receptor, e.g., either species types or cells which lack corresponding antigens and exhibit negative background activity. Expression of transformed genes will allow isolation of antigenically pure cell lines, with defined or single specie variants. This approach will allow for more sensitive detection and discrimination of the physiological effects of chemokine or receptor proteins. Subcellular fragments, e.g., cytoplasts or membrane fragments, can be isolated and used.

Dissection of critical structural elements which effect the various differentiation functions provided by ligands is possible using standard techniques of modern molecular biology, particularly in comparing members of the related class. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390.

In addition, various segments can be substituted between species variants to determine what structural features are important in both receptor binding affinity and specificity, as well as signal transduction. An array of different chemokine or receptor variants will be used to screen for variants exhibiting combined properties of interaction with different species variants.

Intracellular functions would probably involve segments of the receptor which are normally accessible to the cytosol. However, ligand internalization may occur under certain circumstances, and interaction between intracellular components and "extracellular" segments may occur. The specific segments of interaction of a particular chemokine with other intracellular components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolatable by affinity methods or by genetic means, e.g., complementation analysis of mutants.

Further study of the expression and control of the various chemokines or receptors will be pursued. The controlling elements associated with the proteins may exhibit differential developmental, tissue specific, or other expression patterns. Upstream or downstream genetic regions, e.g., control elements, are of interest. Differential splicing of message may lead to membrane bound forms, soluble forms, and modified versions of ligand.

Structural studies of the proteins will lead to design of new ligands or receptors, particularly analogs exhibiting agonist or antagonist properties on the receptor. This can be combined with previously described screening methods to isolate ligands exhibiting desired spectra of activities.

Expression in other cell types will often result in glycosylation differences in a particular chemokine or receptor. Various species variants may exhibit distinct functions based upon structural differences other than amino acid sequence. Differential modifications may be responsible for differential function, and elucidation of the effects are now made possible.

Thus, the present invention provides important reagents related to a physiological ligand-receptor interaction. Although the foregoing description has focused primarily upon the mouse and human embodiments of the chemokines or receptors specifically described, those of skill in the art will immediately recognize that the invention provides other counterparts, e.g., from related species, rodents or primates.

V. Antibodies

Antibodies can be raised to these chemokines or receptors, including species or polymorphic variants, and fragments thereof, both in their naturally occurring forms and in their recombinant forms. Additionally, antibodies can be raised to chemokines or receptors in either their active or inactive forms, or in their native or denatured forms. Anti-idiotypic antibodies are also contemplated.

Methods of producing polyclonal antibodies are well known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the CTACK protein or peptide of interest. For example, when appropriately high titers of antibody to the immunogen are obtained, usually after repeated immunizations, blood is collected from the animal and antisera are prepared. Further fractionation of the antisera to enrich for antibodies reactive to the protein can be performed, if desired. See, e.g., Harlow and Lane *Antibodies, A Laboratory Manual*; or Coligan (ed.) *Current Protocols in Immunology*. Immunization can also be performed through other methods, e.g., DNA vector immunization. See, e.g., Wang, et al. (1997) *Virology* 228:278–284.

Monoclonal antibodies may be obtained by various techniques familiar to those skilled in the art. Typically, spleen cells from an animal immunized with a desired antigen are immortalized, commonly by fusion with a myeloma cell. See, Kohler and Milstein (1976) *Eur. J. Immunol.* 6:511–519. Alternative methods of immortalization include transformation with Epstein Barr Virus, oncogenes, or retroviruses, or other methods known in the art. See, e.g., Doyle, et al. (eds. 1994 and periodic supplements) *Cell and Tissue Culture: Laboratory Procedures*, John Wiley and Sons, New York, N.Y. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) *Science* 246:1275–1281.

Antibodies, including binding fragments and single chain versions, against predetermined fragments of the ligands can be raised by immunization of animals with concatemers or conjugates of the fragments with immunogenic proteins. Monoclonal antibodies are prepared from cells secreting the desired antibody. These antibodies can be screened for binding to normal or defective chemokines or receptors, or screened for agonistic or antagonistic activity. These monoclonal antibodies will usually bind with at least a $K_D$ of about 1 mM, more usually at least about 300 µM, typically at least about 10 µM, more typically at least about 30 µM, preferably at least about 10 µM, and more preferably at least about 3 µM or better.

The antibodies, including antigen binding fragments, of this invention can have significant preparative, diagnostic, or therapeutic value. They can be useful to purify or label the desired antigen in a sample, or may be potent antagonists that bind to ligand and inhibit binding to receptor or inhibit the ability of a ligand to elicit a biological response. They also can be useful as non-neutralizing antibodies and can be coupled to, or as fusion proteins with, toxins or radionuclides so that when the antibody binds to antigen, a cell expressing it, e.g., on its surface via receptor, is killed. Further, these antibodies can be conjugated to drugs or other therapeutic agents, either directly or indirectly by means of a linker, and may effect drug targeting. Antibodies to receptors may be more easily used to block ligand binding and/or signal transduction.

The antibodies of this invention can also be useful in diagnostic or reagent purification applications. As capture or non-neutralizing antibodies, they can be screened for ability to bind to the chemokines or receptors without inhibiting ligand-receptor binding. As neutralizing antibodies, they can be useful in competitive binding assays. They will also be useful in detecting or quantifying chemokine or receptors, e.g., in immunoassays. They may be used as purification reagents in immunoaffinity columns or as immunohistochemistry reagents.

Ligand or receptor fragments may be concatenated or joined to other materials, particularly polypeptides, as fused or covalently joined polypeptides to be used as immunogens. Short peptides will preferably be made as repeat structures to increase size. A ligand and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York, and Williams, et al. (1967) *Methods in Immunology and Immunochemistry*, Vol.1, Academic Press, New York, for descriptions of methods of preparing polyclonal antisera. A typical method involves hyperimmunization of an animal with an antigen. The blood of the animal is then collected shortly after the repeated immunizations and the gamma globulin fraction is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256:495–497, which discusses one method of generating monoclonal antibodies. Summarized briefly, this method involves injecting an animal with an immunogen. The animal is then sacrificed and cells taken, e.g., from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance. Large amounts of antibody may be derived from ascites fluid from an animal.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277, 437; 4,275,149; and 4,366,241. Also, recombinant immunoglobulins may be produced, see Cabilly, U.S. Pat. No. 4,816,567; and Queen et al. (1989) *Proc. Nat'l. Acad. Sci.* 86:10029–10033; or made in transgenic mice, see Mendez, et al. (1997) *Nature Genetics* 15:146–156.

The antibodies of this invention can also be used for affinity chromatography in isolating the protein. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified chemokine protein will be released.

The antibodies may also be used to screen expression libraries for particular expression products. Usually the antibodies used in such a procedure will be labeled with a moiety allowing easy detection of presence of antigen by antibody binding.

Antibodies raised against these chemokines or receptors will also be useful to raise anti-idiotypic antibodies. These will be useful in detecting or diagnosing various immunological conditions related to expression of the respective antigens.

Antibodies are merely one form of specific binding compositions. Other binding compositions, which will often have similar uses, include molecules that bind with specificity to CTACK or Vic receptor, e.g., in a binding partner-binding partner fashion, an antibody-antigen interaction, or in a natural physiologically relevant protein-protein interaction, either covalent or non-covalent, e.g., proteins which specifically associate with CTACK or Vic receptor protein. The molecule may be a polymer, or chemical reagent. A functional analog may be a protein with structural modifications, or may be a structurally unrelated molecule, e.g., which has a molecular shape which interacts with the appropriate binding determinants. Thus, identification of GPR2 as the receptor for CTACK and Vic provides means for producing such a binding composition.

Drug screening using antibodies, CTACK, Vic, or fragments thereof can be performed to identify compounds having binding affinity to CTACK, Vic or GPR2, or can block or simulate the natural interaction with ligand. Subsequent biological assays can then be utilized to determine if the compound has intrinsic blocking activity and is therefore an antagonist. Likewise, a compound having intrinsic stimulating activity can signal to the cells, e.g., via the CTACK pathway and is thus an agonist in that it simulates the activity of a ligand. Mutein antagonists may be developed which maintain receptor binding but lack signaling.

Structural studies of the ligands will lead to design of new variants, particularly analogs exhibiting agonist or antagonist properties on the receptor. This can be combined with previously described screening methods to isolate muteins exhibiting desired spectra of activities.

As receptor specific binding molecules are provided, also included are small molecules identified by screening procedures. In particular, it is well known in the art how to screen for small molecules which interfere, e.g., with ligand binding to the receptor, often by specific binding to the receptor and blocking of binding by natural ligand. See, e.g., meetings on High Throughput Screening, International Business Communications, Southborough, Mass. 01772-1749. Such molecules may compete with natural ligands, and selectively bind to the CTACK, Vic, or GPR2.

VI. Nucleic Acids

The described peptide sequences and the related reagents are useful in isolating a DNA clone encoding these chemokines or receptors, e.g., from a natural source. Typically, it will be useful in isolating a gene from another individual, and similar procedures will be applied to isolate genes from related species, e.g., rodents or primates. Cross hybridization will allow isolation of ligand from other closely related species. A number of different approaches should be available to successfully isolate a suitable nucleic acid clone. Similar concepts apply to the receptor embodiments.

The purified protein or defined peptides are useful for generating antibodies by standard methods, as described above. Synthetic peptides or purified protein can be presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. Alternatively, a chemokine or receptor may be used as a specific binding reagent, and advantage can be taken of its specificity of binding, much like an antibody would be used. The chemokine receptors are typically 7 transmembrane proteins, which could be sensitive to appropriate interaction with lipid or membrane. The signal transduction typically is mediated through a G-protein, through interaction with a G-protein coupled receptor.

For example, the specific binding composition could be used for screening of an expression library made from a cell line which expresses a particular chemokine. The screening can be standard staining of surface expressed ligand, or by panning. Screening of intracellular expression can also be performed by various staining or immunofluorescence procedures. The binding compositions could be used to affinity purify or sort out cells expressing the ligand.

The peptide segments can also be used to predict appropriate oligonucleotides to screen a library, e.g., to isolate species variants. The genetic code can be used to select appropriate oligonucleotides useful as probes for screening. See, e.g., SEQ ID NO: 2, 4, 6, 8, 10, 12, or 14. In combination with polymerase chain reaction (PCR) techniques, synthetic oligonucleotides will be useful in selecting correct clones from a library. Complementary sequences will also be used as probes or primers. Anchored vector or poly-A complementary PCR techniques or complementary DNA of other peptides may be useful.

This invention contemplates use of isolated DNA or fragments to encode a biologically active corresponding chemokine polypeptide. In addition, this invention covers isolated or recombinant DNA which encodes a biologically active protein or polypeptide which is capable of hybridizing under appropriate conditions with the DNA sequences described herein. Said biologically active protein or polypeptide can be an intact ligand. receptor, or fragment, and have an amino acid sequence as disclosed in SEQ ID NO: 2, 4, 6, 8, 10, 12, and 14. Further, this invention covers the use of isolated or recombinant DNA, or fragments thereof, which encode proteins which are homologous to a chemokine or receptor or which was isolated using such a cDNA encoding a chemokine or receptor as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring purified forms. Thus, for example, products made by transforming cells with any unnaturally occurring vector is encompassed, as are nucleic acids comprising sequence derived using a synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least about 20 nucleotides, more generally at least about 23 nucleotides, ordinarily at least about 26 nucleotides, more ordinarily at least about 29 nucleotides, often at least about 32 nucleotides, more often at least about 35 nucleotides, typically at least about 38 nucleotides, more typically at least about 41 nucleotides, usually at least about 44 nucleotides, more usually at least about 47 nucleotides, preferably at least about 50 nucleotides, more preferably at least about 53 nucleotides, and in particularly preferred embodiments will be at least about 56 or more nucleotides, e.g., 60, 65, 75, 85, 100, 120, 150, 200, 250, 300, 400, etc. Such fragments may have ends which begin and/or end at virtually all positions, e.g., beginning at nucleotides 1, 2, 3, etc., and ending at, e.g., 300, 299, 298, 287, etc., in combinatorial pairs. Particularly interesting polynucleotides have ends corresponding to structural domain boundaries.

A DNA which codes for a particular chemokine or receptor protein or peptide will be very useful to identify genes, mRNA, and cDNA species which code for related or homologous ligands or receptors, as well as DNAs which code for homologous proteins from different species. There are likely homologs in closely related species, e.g., rodents or primates. Various chemokine proteins should be homologous and are encompassed herein, as would be receptors. However, proteins can readily be isolated under appropriate conditions using these sequences if they are sufficiently homologous. Typically, primate chemokines or receptors are of particular interest.

This invention further covers recombinant DNA molecules and fragments having a DNA sequence identical to or highly homologous to the isolated DNAs set forth herein. In particular, the sequences will often be operably linked to DNA segments which control transcription, translation, and DNA replication. Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology* Academic Press, San Diego, pp.1502–1504; Travis (1992) *Science* 256:1392–1394; Kuhn, et al. (1991) *Science* 254:707–710; Capecchi (1989) *Science* 244:1288; Robertson (1987)(ed.) *Teratocarcinomas and Embryonic Stem Cells: A Practical Approach* IRL Press, Oxford; and Rosenberg (1992) *J. Clinical Oncology* 10:180–199.

Homologous nucleic acid sequences, when compared, exhibit significant similarity, or identity. The standards for homology in nucleic acids are either measures for homology generally used in the art by sequence comparison or based upon hybridization conditions. The hybridization conditions are described in greater detail below.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least about 56%, more generally at least about 59%, ordinarily at least about 62%, more ordinarily at least about 65%, often at least about 68%, more often at least about 71%, typically at least about 74%, more typically at least about 77%, usually at least about 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a sequence derived from SEQ ID NO:1, 3, 5, 7, 9, 11, or 13. Typically, selective hybridization will occur when there is at least about 55% homology over a stretch of at least about 30 nucleotides, preferably at least about 65% over a stretch of at least about 25 nucleotides, more preferably at least about 75%, and most preferably at least about 90% over about 20 nucleotides. See, Kanehisa (1984) *Nuc. Acids Res.* 12:203–213. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides. PCR primers will generally have high levels of matches over potentially shorter lengths.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM, e.g., 20–50 mM. However, the combination of parameters is much more important than the measure of any single parameter. See, e.g., Wetmur and Davidson (1968) *J. Mol. Biol.* 31:349–370.

Corresponding chemokines or receptors from other closely related species can be cloned and isolated by cross-species hybridization. Alternatively, sequences from a sequence data base may be recognized as having similarity. Homology may be very low between distantly related species, and thus hybridization of relatively closely related species is advisable. Alternatively, preparation of an antibody preparation which exhibits less species specificity may be useful in expression cloning approaches. PCR approaches using segments of conserved sequences will also be used.

VII. Making Chemokines or Receptors; Mimetics

DNA which encodes each respective chemokine, receptor, or fragments thereof can be obtained by chemical synthesis, screening cDNA libraries, or by screening genomic libraries prepared from a wide variety of cell lines or tissue samples.

This DNA can be expressed in a wide variety of host cells for the synthesis of a full-length ligand or fragments which can in turn, for example, be used to generate polyclonal or monoclonal antibodies; for binding studies; for construction and expression of modified molecules; for expression cloning or purification; and for structure/function studies. Each antigen or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigens or antibodies, or portions thereof, may be expressed as fusions with other proteins.

Expression vectors are typically self-replicating DNA or RNA constructs containing the desired antigen gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention contain DNA which encode embodiments of a chemokine, receptor, or a fragment thereof, typically encoding a biologically active polypeptide. The DNA can be under the control of a viral promoter and can encode a selection marker. This invention further contemplates use of such expression vectors which are capable of expressing eukaryotic cDNA coding for each chemokine or receptor in a prokaryotic or eukaryotic host, where the vector is compatible with the host and where the eukaryotic cDNA coding for the protein is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the ligand or its fragments in various hosts using vectors that do not contain a replication origin that is recognized by the host cell. It is also possible to use vectors that cause integration of a chemokine or receptor gene or its fragments into the host DNA by recombination, or to integrate a promoter which controls expression of an endogenous gene.

Vectors, as used herein, comprise plasmids, viruses, bacteriophage, integratable DNA fragments, and other vehicles, including those which enable the integration of DNA fragments into the genome of the host. Expression vectors are specialized vectors which contain genetic control elements that effect expression of operably linked genes. Plasmids are the most commonly used form of vector but many other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y., and Rodriquez, et al. (1988)(eds.) *Vectors: A Survey of Molecular Cloning Vectors and Their Uses*, Buttersworth, Boston, Mass.

Transformed cells include cells, preferably mammalian, that have been transformed or transfected with a chemokine or receptor gene containing vector constructed using recombinant DNA techniques. Transformed host cells usually express the ligand, receptor, or its fragments, but for purposes of cloning, amplifying, and manipulating its DNA, do not need to express the protein. This invention further contemplates culturing transformed cells in a nutrient medium, thus permitting the protein to accumulate in the culture. The protein can be recovered, from the culture or from the culture medium, or from cell membranes.

For purposes of this invention, DNA sequences are operably linked when they are functionally related to each other. For example, DNA for a presequence or secretory signal is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express these chemokines or their fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses*, Buttersworth, Boston, Chapter 10, pp. 205–236.

Lower eukaryotes, e.g., yeasts and *Dictyostelium*, may be transformed with chemokine or receptor sequence containing nucleic acids. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the functionally active chemokine or receptor proteins. In principle, most any higher eukaryotic tissue culture cell line is workable, e.g., insect baculovirus expression systems, whether from an invertebrate or vertebrate source. However, mammalian cells are preferred, in that the processing, both cotranslationally and posttranslationally, will be typically most like natural. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610.

It will often be desired to express a chemokine or receptor polypeptide in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, a chemokine or receptor gene may be co-transformed with one or more genes encoding mammalian or other glycosylating enzymes. Using this approach, certain mammalian glycosylation patterns will be achievable or approximated in prokaryote or other cells.

A chemokine, receptor, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

Now that these chemokines and receptors have been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexyl-carbodiimide (DCCD)/additive process can be used. Solid phase and solution phase syntheses are both applicable to the foregoing processes.

These chemokines, receptors, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction are typically protected to prevent coupling at an incorrect location.

If a solid phase synthesis is adopted, the C-terminal amino acid is typically bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonyl-hydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described, e.g., by Merrifield, et al. (1963) in *J. Am. Chem. Soc.* 85:2149–2156.

The prepared ligand and fragments thereof can be isolated and purified from the reaction mixture by means of peptide separation, e.g., by extraction, precipitation, electrophoresis, and various forms of chromatography, and the like. The various chemokines or receptors of this invention can be obtained in varying degrees of purity depending upon its desired use. Purification can be accomplished by use of the protein purification techniques disclosed herein or by the use of the antibodies herein described, e.g., in immunoabsorbant affinity chromatography. This immunoabsorbant affinity chromatography is typically carried out, e.g., by first linking the antibodies to a solid support and then contacting the linked antibodies with solubilized lysates of appropriate source cells, lysates of other cells expressing the ligand or receptor, or lysates or supernatants of cells producing the desired proteins as a result of DNA techniques, see below.

VIII. Uses

The present invention provides reagents which will find use in diagnostic applications as described elsewhere herein, e.g., in the general description for developmental abnormalities, or below in the description of kits for diagnosis. In particular, it appears that the GPR2 is selectively expressed on the Th2 T cell subset. This suggests that the reagents described herein may be valuable in defining Th2 or Th1 diseases, or in treating the respective disease types by acting on the selective T cell subsets. See, e.g., Romagnani (1997) *Current Op. Immunology* 9:773–775; Romagnani (1997) *The Th1/Th2 Paradigm in Disease* Springer-Verlag and Landes, Austin, Tex.

Because Vic is a pro-inflammatory chemokine, antagonists should block such a response. Both Vic and CTACK are found in skin, so antagonists may be useful in blocking skin inflammation. The chemokines may be useful in attracting GPR2+ cells, and may be useful as tumor or immune adjuvants, including cutaneos adjuvants.

Thus, depletion of Th2 subsets in a Th2 mediated disease may prevent or ameliorate symptoms. Conversely, supplementing the Th2 subsets in a Th1 mediated disease may be efficacious, e.g., by inhibiting the Th1 subset. In particular, asthmatic or allergic reactions may be regulated using the methods of the present invention.

This invention also provides reagents with significant therapeutic potential. These chemokines and receptors (naturally occurring or recombinant), fragments thereof, and binding compositions, e.g., antibodies thereto, along with compounds identified as having binding affinity to them, should be useful in the treatment of conditions associated with abnormal physiology or development, including inflammatory conditions, e.g., asthma. In particular, modulation of trafficking of leukocytes is one likely biological activity, but a wider tissue distribution might suggest broader biological activity, including, e.g., antiviral effects. Abnormal proliferation, regeneration, degeneration, and atrophy may be modulated by appropriate therapeutic treatment using the compositions provided herein. For example, a disease or disorder associated with abnormal expression or abnormal signaling by a chemokine or ligand for a receptor should be a likely target for an agonist or antagonist of the ligand.

Various abnormal physiological or developmental conditions are known in cell types shown to possess the chemokine or receptor mRNAs by Northern blot analysis. See Berkow (ed.) *The Merck Manual of Diagnosis and Therapy*, Merck & Co., Rahway, N.J.; and Thorn, et al. *Harrison's Principles of Internal Medicine*, McGraw-Hill, N.Y. Developmental or functional abnormalities, e.g., of the immune system, cause significant medical abnormalities and conditions which may be susceptible to prevention or treatment using compositions provided herein. The present invention teaches various skin related diseases as conditions susceptible to analysis or diagnosis by evaluating CTACK, Vic, or GPR2. For example, the likelihood of skin rejection in a graft situation would be evaluated by the amount of CTACK and/or Vic present. Prophylactic downregulation may be useful to prevent the recruitment of dermal T or NK cells. Response to various skin tumors may be evaluated by the presence or absence of CTACK and/or Vic.

Antibodies to the chemokines or receptors, including recombinant forms, can be purified and then used diagnostically or therapeutically, alone or in combination with other chemokines, cytokines, or antagonists thereof. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding. Moreover, modifications to the antibody molecules or antigen binding fragments thereof, may be adopted which affect the pharmacokinetics or pharmacodynamics of the therapeutic entity.

Drug screening using antibodies or receptor or fragments thereof can be performed to identify compounds having binding affinity to each chemokine or receptor, including isolation of associated components. Subsequent biological assays can then be utilized to determine if the compound has intrinsic stimulating activity and is therefore a blocker or antagonist in that it blocks the activity of the ligand. Likewise, a compound having intrinsic stimulating activity can activate the receptor and is thus an agonist in that it simulates the activity of a ligand. This invention further contemplates the therapeutic use of antibodies to these chemokines as antagonists, or to the receptors as antagonists or agonists. This approach should be particularly useful with other chemokine or receptor species variants.

The quantities of reagents necessary for effective therapy will depend upon many different factors, including means of administration, target site, physiological state of the patient, and other medicants administered. Thus, treatment dosages should be titrated to optimize safety and efficacy in various populations, including racial subgroups, age, gender, etc. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds. 1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers typically include water, saline, buffers, and other compounds described, e.g., in the Merck Index, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

Selecting an administration regimen for a therapeutic agonist or antagonist depends on several factors, including the serum or tissue turnover rate of the therapeutic, the immunogenicity of the therapeutic, or the accessibility of the target cells. Preferably, an administration regimen maximizes the amount of therapeutic delivered to the patient consistent with an acceptable level of side effects. Accordingly, the amount of therapeutic delivered depends in part on the particular agonist or antagonist and the severity of the condition being treated. Guidance in selecting appropriate doses of antibodies is found in the literature on therapeutic uses, e.g. Bach et al., chapter 22, in Ferrone, et al. (eds. 1985), *Handbook of Monoclonal Antibodies* Noges Publications, Park Ridge, N.J.; and Russell, pgs. 303–357, and Smith et al., pgs. 365–389, in Haber, et al. (eds. 1977) *Antibodies in Human Diagnosis and Therapy* Raven Press, New York, N.Y.

Determination of the appropriate dose is made by the clinician, e.g., using parameters or factors known in the art to affect treatment or predicted to affect treatment. Generally, the dose begins with an amount somewhat less than the optimum dose and it is increased by small increments thereafter until the desired or optimum effect is achieved relative to any negative side effects. CLA+ cell levels might be important indicators of when an effective dose is reached. Preferably, an antibody or binding composition thereof that will be used is derived from the same species as the animal targeted for treatment, thereby minimizing a humoral response to the reagent.

The total weekly dose ranges for antibodies or fragments thereof, which specifically bind to CTACK, range generally from about 1 ng, more generally from about 10 ng, typically from about 100 ng; more typically from about 1 $\mu$g, more typically from about 10 $\mu$g, preferably from about 100 $\mu$g, and more preferably from about 1 mg per kilogram body weight. Although higher amounts may be more efficacious, the lower doses typically will have fewer adverse effects. Generally the range will be less than 100 mg, preferably less than about 50 mg, and more preferably less than about 25 mg per kilogram body weight.

The weekly dose ranges for antagonists, e.g., antibody, binding fragments, range from about 10 $\mu$g, preferably at least about 50 μg, and more preferably at least about 100 μg per kilogram of body weight. Generally, the range will be less than about 1000 μg, preferably less than about 500 μg, and more preferably less than about 100 μg per kilogram of body weight. Dosages are on a schedule which effects the desired treatment and can be periodic over shorter or longer term. In general, ranges will be from at least about 10 μg to about 50 mg, preferably about 100 μg to about 10 mg per kilogram body weight.

Other antagonists of the ligands, e.g., muteins, are also contemplated. Hourly dose ranges for muteins range from at least about 10 μg, generally at least about 50 μg, typically at least about 100 g, and preferably at least 500 g per hour. Generally the dosage will be less than about 100 mg, typically less than about 30 mg, preferably less than about 10 mg, and more preferably less than about 6 mg per hour. General ranges will be from at least about 1 μg to about 1000 μg, preferably about 10 μg to about 500 μg per hour.

In particular contexts, e.g., transplant or skin grafts, may involve the administration of the therapeutics in different forms. For example, in a skin graft, the tissue may be immersed in a sterile medium containing the therapeutic resulting in a prophylactic effect on cell migration soon after the graft is applied.

A chemokine, fragments thereof, or antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is often preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Carriers may improve storage life, stability, etc. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds. 1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; Avis, et al. (eds. 1993) *Pharmaceutical Dosage Forms: Parenteral Medications* Dekker, N.Y.; Lieberman, et al. (eds. 1990) *Pharmaceutical Dosage Forms: Tablets* Dekker, N.Y.; and Lieberman, et al. (eds. 1990) *Pharmaceutical Dosage Forms: Disperse Systems* Dekker, N.Y. The therapy of this invention may be combined with or used in association with other therapeutic agents. Similar considerations will often apply to receptor based reagents.

The present invention also provides for administration of CTACK, Vic, or GPR2 antibodies or binding compositions in combination with known therapies, e.g., steroids, particularly glucocorticoids, which alleviate the symptoms associated with excessive inflammatory responses. Daily dosages for glucocorticoids will range from at least about 1 mg, generally at least about 2 mg, and preferably at least about 5 mg per day. Generally, the dosage will be less than about 100 mg, typically less than about 50 mg, preferably less than about 20 mg, and more preferably at least about 10 mg per day. In general, the ranges will be from at least about 1 mg to about 100 mg, preferably from about 2 mg to 50 mg per day.

The phrase "effective amount" means an amount sufficient to effect a desired response, or to ameliorate a symptom or sign of the skin condition. Typical mammalian hosts will include mice, rats, cats, dogs, and primates, including humans. An effective amount for a particular patient may vary depending on factors such as the condition being treated, the overall health of the patient, the method, route, and dose of administration and the severity of side affects. Preferably, the effect will result in a change in quantitation of at least about 10%, preferably at least 20%, 30%, 50%, 70%, or even 90% or more. When in combination, an effective amount is in ratio to a combination of components and the effect is not limited to individual components alone.

An effective amount of therapeutic will modulate the symptoms typically by at least about 10%; usually by at least about 20%; preferably at least about 30%; or more preferably at least about 50%. Alternatively, modulation of movement will mean that the movement or trafficking of various cell types is affected. Such will result in, e.g., statistically significant and quantifiable changes in the numbers of cells being affected. This may be an increase or decrease in the numbers of target cells being attracted within a time period or target area.

The present invention provides reagents which will find use in therapeutic applications as described elsewhere herein, e.g., in the general description for treating disorders associated with skin conditions. See, e.g., Berkow (ed.) *The Merck Manual of Diagnosis and Therapy*, Merck & Co., Rahway, N.J.; Thorn, et al. *Harrison's Principles of Internal Medicine*, McGraw-Hill, NY; Gilman, et al. (eds. 1990) *Goodman and Gilman's: The Pharmacological Bases of Therapeutics*, 8th Ed., Pergamon Press; *Remington's Pharmaceutical Sciences*, 17th ed. (1990), Mack Publishing Co., Easton, Pa.; Langer (1990) *Science* 249:1527–1533; and *Merck Index*, Merck & Co., Rahway, N.J.

Both the naturally occurring and the recombinant forms of the chemokines or receptors of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate. The development of suitable assays can be greatly facilitated by the availability of large amounts of purified, soluble chemokine as provided by this invention.

For example, antagonists can normally be found once a ligand has been structurally defined. Testing of potential ligand analogs is now possible upon the development of highly automated assay methods using physiologically responsive cells. In particular, new agonists and antagonists will be discovered by using screening techniques described herein.

Viable cells could also be used to screen for the effects of drugs on respective chemokine or G-protein coupled receptor mediated functions, e.g., second messenger levels, i.e., $Ca^{++}$; inositol phosphate pool changes (see, e.g., Berridge (1993) *Nature* 361:315–325 or Billah and Anthes (1990) *Biochem. J.* 269:281–291); cellular morphology modification responses; phosphoinositide lipid turnover; an antiviral response, and others. Some detection methods allow for elimination of a separation step, e.g., a proximity sensitive detection system. Calcium sensitive dyes will be useful for detecting Ca$^{++}$ levels, with a fluorimeter or a fluorescence cell sorting apparatus.

Rational drug design may also be based upon structural studies of the molecular shapes of the chemokines, other effectors or analogs, or the receptors. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York.

Purified chemokine or receptor can be coated directly onto plates for use in the aforementioned drug screening techniques, and may be associated with detergents or lipids. However, non-neutralizing antibodies, e.g., to the chemokines or receptors can be used as capture antibodies to immobilize the respective protein on the solid phase.

Because Vic and CTACK bind to certain cell surfaces (e.g., see below), the purfied ehcmokine may also be administered while it is bound to an extracellular matrix (ECM). The ECM:chemokine complex may allow slower diffusion and thus sustained release of the chemokine.

Similar concepts also apply to the chemokine receptor embodiments of the invention.

IX. Kits

This invention also contemplates use of chemokine or receptor proteins, fragments thereof, peptides, binding compositions, and their fusion products in a variety of diagnostic kits and methods for detecting the presence of ligand, antibodies, or receptors. Typically the kit will have a compartment containing a defined chemokine or receptor peptide or gene segment or a reagent which recognizes one or the other, e.g., binding reagents.

A kit for determining the binding affinity of a test compound to a chemokine or receptor would typically comprise a test compound; a labeled compound, for example an antibody having known binding affinity for the protein; a source of chemokine or receptor (naturally occurring or recombinant); and a means for separating bound from free labeled compound, such as a solid phase for immobilizing the ligand or receptor. Once compounds are screened, those having suitable binding affinity to the ligand or receptor can be evaluated in suitable biological assays, as are well known in the art, to determine whether they act as agonists or antagonists to the receptor. The availability of recombinant chemokine or receptor polypeptides also provide well defined standards for calibrating such assays or as positive control samples.

A preferred kit for determining the concentration of, for example, a chemokine or receptor in a sample would typically comprise a labeled compound, e.g., antibody, having known binding affinity for the target, a source of ligand or receptor (naturally occurring or recombinant) and a means for separating the bound from free labeled compound, for example, a solid phase for immobilizing the chemokine or receptor. Compartments containing reagents, and instructions for use or disposal, will normally be provided.

Antibodies, including antigen binding fragments, specific for the chemokine or receptor, or fragments are useful in diagnostic applications to detect the presence of elevated levels of chemokine, receptor, and/or its fragments. Such diagnostic assays can employ lysates, live cells, fixed cells, immunofluorescence, cell cultures, body fluids, and further can involve the detection of antigens related to the ligand or receptor in serum, or the like. Diagnostic assays may be homogeneous (without a separation step between free reagent and antigen complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the primary antibody to a chemokine or receptor or to a particular fragment thereof. Similar assays have also been extensively discussed in the literature. See, e.g., Harlow and Lane (1988) *Antibodies: A Laboratory Manual*, CSH.

Anti-idiotypic antibodies may have similar uses to diagnose presence of antibodies against a chemokine or receptor, as such may be diagnostic of various abnormal states. For example, overproduction of a chemokine or receptor may result in production of various immunological reactions which may be diagnostic of abnormal physiological states, particularly in various inflammatory or asthma conditions.

Frequently, the reagents for diagnostic assays are supplied in kits, so as to optimize the sensitivity of the assay. For the subject invention, depending upon the nature of the assay, the protocol, and the label, either labeled or unlabeled antibody or labeled chemokine or receptor is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments or containers for each useful reagent. Desirably, the reagents are provided as a dry lyophilized powder, where the reagents may be reconstituted in an aqueous medium providing appropriate concentrations of reagents for performing the assay.

The aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the ligand, test compound, chemokine, receptor, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating bound from the free ligand, or alternatively bound from free test compound. The chemokine or receptor can be immobilized on various matrixes, perhaps with detergents or associated lipids, followed by washing. Suitable matrixes include plastic such as an ELISA plate, filters, and beads. Methods of immobilizing the chemokine or receptor to a matrix include, without limitation, direct adhesion to plastic, use of a capture antibody, chemical coupling, and biotin-avidin. The last step in this approach may involve the precipitation of antigen/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of the chemokine or receptor. These sequences can be used as probes for detecting levels of the ligand message in samples from patients suspected of having an abnormal condition, e.g., an inflammatory, physiological, or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

X. Receptor; Ligands for Receptors

Having identified a ligand binding partner of a specific interaction, methods exist for isolating the counter-partner. See, Gearing, et al *EMBO J.* 8:3667–4676 or McMahan, et al. (1991) *EMBO J.* 10:2821–2832. For example, means to label a chemokine without interfering with the binding to its receptor can be determined. For example, an affinity label can be fused to either the amino- or carboxy-terminus of the ligand. An expression library can be screened for specific binding of chemokine, e.g., by cell sorting, or other screening to detect subpopulations which express such a binding component. See, e.g., Ho, et al. (1993) *Proc. Nat'l Acad. Sci.* 90:11267–11271. Alternatively, a panning method may be used. See, e.g., Seed and Aruffo (1987) *Proc. Nat'l. Acad. Sci.* 84:3365–3369.

With a receptor, means to identify the ligand exist. Methods for using the receptor, e.g., on the cell membrane, can be used to screen for ligand by, e.g., assaying for a common G-protein linked signal such as Ca++ flux. See Lerner (1994) *Trends in Neurosciences* 17:142–146. It is likely that the ligands for these receptors are chemokines.

Protein cross-linking techniques with label can be applied to a isolate binding partners of a chemokine. This would allow identification of protein which specifically interacts with a chemokine, e.g., in a ligand-receptor like manner.

The broad scope of this invention is best understood with reference to the following examples, which are not intended to limit the invention to specific embodiments.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols. 1–3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York; Innis, et al. (eds.)(1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology*, vol. 182, and other volumes in this series; manufacturer's literature on use of protein purification products, e.g., Pharmacia, Piscataway, N.J., or Bio-Rad, Richmond, Calif.; and Coligan, et al. (eds.) (1995 and periodic supplements) *Current Protocols in Protein Science*, John Wiley & Sons, New York, N.Y. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *QIAexpress: The High Level Expression & Protein Purification System* QIAGEN, Inc., Chatsworth, Calif.

Standard immunological techniques are described, e.g., in Hertzenberg, et al. (eds. 1996) *Weir's Handbook of Experimental Immunology* vols. 1–4, Blackwell Science; Coligan (1991) *Current Protocols in Immunology* Wiley/Greene, NY; and *Methods in Enzymology* volumes. 70, 73, 74, 84, 92, 30 93, 108, 116, 121,132, 150, 162, and 163.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Cell Culture and Tissue Samples

Adult human primary cells including keratinocytes, melanocytes, and dermal fibroblasts were obtained from Clonetics and cultured according to the suppliers instructions. The T cell line, 7–17, was kindly provided by Richard Boismenu (The Scripps Institute, La Jolla, Calif.). For cytokine treatment, cells were cultured with 10 ng/ml hTNF-α plus 3 ng/ml hIL-1 (R&D Systems) in culture medium for the indicated times. Mouse ear skin from BALB/c mice was separated into epidermis and dermis following incubation with 2.5% trypsin in PBS for 30 min at 37° C. Human PBMC were obtained from healthy donors by erythrocyte sedimentation followed by Ficoll-Histopaque-1077 (Sigma Chem. Co.) sedimentation. Human T cells were purified from PBMCs using a T-cell enrichment column (R&D Systems) according to the manufacturers instructions.

III. Isolation of CTACK, Vic, or GPR2 Encoding Sequences

The human or mouse ClACK sequence is readily available. See SEQ ID NO: 11 or 13, respectively. Appropriate PCR primers or hybridization probes can be selected. Likewise for GPR2 and Vic (SEQ ID NO: 1,3, 5, 7, and 9) sequence analysis. TBLASTN searches of a proprietary and Genbank dbEST databases, with the sequences of known CC chemokines, identified the ESTs for human and murine CTACK. respectively. Murine CTACK cDNA, IMAGE consortium clone #316475, was obtained from Genome Systems as an EcoRI-NotI insert in the pT7T3-PacD vector. Human CTACK was obtained as a SalI-NotI insert in the pSPORT 3.0 vector. The nucleotide sequence of both clones was confirmed by automated sequencing. The signal peptide cleavage sites were predicted using the SignalP server. Sequences were aligned using CLUSTAL W.

The GPR2 was isolated from a cDNA library made from a human cDNA library. A partial sequence was reported by Marchese, et al. (1994) *Genomics* 23:609–618. Individual cDNA clones are sequenced using standard methods, e.g., the Taq DyeDeoxy Terminator Cycle Sequencing kit (Applied Biosystems, Foster City, Calif.), and the sequence further characterized.

Other rodent counterparts have been isolated and described. A Southern blot may indicate the extent of homology across species, and either a cDNA library or mRNA can be screened to identify an appropriate cell source. The physiological state of many different cell types may also be evaluated for increased expression of the gene.

Computer analysis suggests that the closest related genes are various G-protein coupled receptors. These include the chemokine receptors, and protease, e.g., thrombin, receptors. Structural motifs suggest that the receptor may contain motifs characteristic of the chemokine receptor family, and of the protease receptor family. Hydrophobicity plots and comparisons with other similar GPCRs should allow prediction of the transmembrane segments. See, e.g., Loetscher, et al. (1996) *J. Expt'l Med.* 184:963–969. A computer analysis of GPCR sequences will indicate residues characteristic of the family members.

Other primate counterparts should be isolatable using the entire coding portion of this human clone as a hybridization probe. A Southern blot may indicate the extent of homology across species, and either a cDNA library or mRNA can be screened to identify an appropriate cell source. The physiological state of many different cell types may also be evaluated for increased expression of the gene.

Chemokine receptors are generally considered useful targets for novel drug discovery, where the therapeutics would agonise or antagonise the binding of natural ligand(s) of the receptor. These receptor-ligand interactions may result in inflammation, cell recruitment, an/or cell activation processes. The GPR2 is upregulated in Hashimoto's thyroiditis and psoriasis.

Some of these receptors are the portal of entry of infectious agents, e.g., viruses. Therefore, therapeutics directed against the chemokine receptor may find application in these diseases. In addition, the receptors may be important in determining fundamental structure or physiological responses.

Other species counterparts should be isolatable using the entire coding portion of these clones as a hybridization probe. A Southern blot may indicate the extent of homology across species, and either a cDNA library or mRNA can be screened to identify an appropriate cell source. The physiological state of many different cell types may also be evaluated for increased expression of the gene.

IV. Chromosome Mapping

The cDNA is labeled, e.g., nick-translated with biotin-14 dATP and hybridized in situ at a final concentration of 5 ng/$\mu$l to metaphases from two normal males. Fluorescence in situ hybridization (FISH) method may be modified from that described by Callen, et al. (1990). *Ann. Genet.* 33:219–221, in that chromosomes are stained before analysis with both propidium iodide (as counter stain) and DAPI (for chromosome identification). Images of metaphase preparations are captured by a CCD camera and computer enhanced. Identification of the appropriate labeled chromosomes is determined.

CTACK was placed on mouse chromosome 4 by interspecific backcross analysis essentially as described in Kelner, et al. (1994) *Science* 266:1395–1399, except that in this case an ~400 bp EcoRI/NotI fragment of mouse CTACK cDNA was used for Southern blotting. Fragments of 14.5 and 8.9 kb were detected in BgII digested C57BL/6J DNA and fragments of 8.9 and 4.4 kb were detected in BgII digested *M. spretus* DNA. The presence or absence of the 4.4 kb BgII-specific fragment was followed in backcross mice. Recombination distances were calculated using Map Manager, version 2.6.5.

mCTACK maps in the proximal region of mouse chromosome 4. CTACK was placed on mouse chromosome 4 by interspecific backcross analysis. More than 98 animals were typed. A search of Genbank with the sequence of hCTACK revealed that the gene for hCTACK overlaps with the extreme 3' end (after the poly A signal) of the IL-11 receptor $\alpha$ chain gene, but on the opposite strand. IL-11R$\alpha$ chain is located on chromosome 9p13, a region syntenic with the proximal arm of mouse chromosome 4.

Similar methods can be used to map Vic and GPR2.

V. Distribution Analysis

For Southern blotting, 5 g of each cDNA library was digested with the appropriate restriction enzymes to release the insert, subjected to gel electrophoresis, and transferred to Hybond-N$^+$ membrane. For Northern blotting all RNAs were isolated using RNAzol B (TEL-TEST, Inc.) and analyzed by electrophoresis on a 1% formaldehyde-agarose gel and transferred to Hybond-N$^+$ membrane. Northern and Southern blots were hybridized for 16 hr at 65° C. with $^{32}$P-labeled probes obtained by randomly priming (Prime-it; Stratagene) the full length inserts from mouse or human CTACK clones. After hybridization, blots were washed at high stringency and exposed to film.

Southern blot analysis of CTACK expression in cDNA libraries generated from human samples included: fetal kidney, lung and liver, peripheral blood mononuclear cells (PBMC and PBMC-act) resting or activated (act) with anti-CD3 and PMA, and T cells (MOT72 and MOT72-act) resting or activated with anti-CD28 and anti-CD3, GM-CSF plus IL-4-generated dendritic cells, elutriated monocytes activated with LPS, IFN$\gamma$ and either anti-IL-10 or IL-10, A549 (epithelial) cells treated with IL-1$\beta$, adult organs and tissues, diseased and normal.

Northern blot analysis of CTACK expression in mouse tissues and organs included: epidermis and dermis derived from ear skin, liver, spleen, thymus, peripheral lymph nodes (PLN), and ear draining lymph nodes (Auricular LN).

Northern blot analysis of CTACK expression was performed in primary keratinocytes, primary melanocytes, 7–17 cells (γδ T cell line) and primary dermal fibroblasts either untreated or treated with TNF- and IL-1. This, along with RT-PCR results suggested that CTACK RNA is expressed by human keratinocytes and upregulated by pro-inflammatory cytokines.

Alternatively, RNAs were treated with DNaseI and reverse transcribed, and the resulting cDNAs were used as templates for competitive RT-PCR as described. Gilliland, et al. (1990) *Proc. Nat'l Acad. Sci. USA* 87:2725–2729; and Platzer, et al. (1992) *Eur. J. Immunol.* 22:1179–1184. The competitor DNA fragment for CTACK was generated according to Celi, et al. (1993) *Nucleic Acids Res.* 21:1047. The following primers were used to obtain a human CTACK competitor fragment (155 bp): sense primer 5'-CTGTACTCAGCTCTACCGAAAGCC-3' (see position 99–122 of SEQ ID NO: 1); anti-sense primer 5'-GCCCATTTTCCTTAGCATCCCATGCAGATGCTG CGTTGAGC-3' (see position 336–316+ position 233–214 of SEQ ID NO: 1). The competitor fragment for human -actin was kindly provided by Dr. J. Krüssel (Dept. of Gynecology and Obstetrics, Heinrich-Heine-University, Düsseldorf, Germany; Krüssel, et al. (1997) *J. Reprod. Immunol.* 34:103–120). Primer pairs used for competitive PCR were as follows: human CTACK (244 bp) sense primer 5'-CTGTACTCAGCTCTACCGAAAGCC-3' (see position 99–122 of SEQ ID NO: 11); anti-sense primer 5'-GCCCATTTTCCTTAGCATCCC-3' (see position 336–316 of SEQ ID NO: 11); human β-actin sense primer 5'-ATCTGGCACCACACCTTCTACAATGAGCTGCG-3' (see SEQ ID NO: 15); anti-sense primer 5'-CGTCATACTCCTGCTTGCTGATCCACATCTGC-3' (see SEQ ID NO: 16). Competitive RT-PCR products were quantified on digitalized agarose gels using Eagle Eye II image analysis software (Stratagene).

RNA samples were reverse transcribed and used as template to amplify CTACK and β-actin. β-actin was used for normalization of the results, which are compared with β-actin mRNA expression levels.

These expression studies revealed that CTACK is extremely tissue specific. More than 70 human cDNA libraries were probed by Southern blotting, including 46 libraries from hematopoietic and non-hematopoetic cells and 25 libraries from normal tissue and diseased tissue. Essentially, CTACK hybridizes exclusively with libraries derived from normal or psoriatic skin. Southern blotting with murine CTACK reveals no significant hybridization with over 45 mouse libraries derived from a variety of cells and tissues; however, this panel did not include a skin-derived library.

To determine whether murine CTACK is also expressed in skin Northern blot analysis was performed using RNA generated from both the epidermis and the dermis of mouse ear skin or from several other favored organs. An RNA species of 0.8 kb is readily detected in the epidermis, only faintly in the dermis and not at all in the other organs tested. The faint signal in the dermis may be attributed to imperfect separation of the epidermis from the dermis. These results indicate that CTACK expression is not only highly tissue-specific, but its selective expression in the skin is restricted to the epidermis. This is in contrast to other chemokines such as IP-10 and IL-8 which are expressed in skin (Schroder (1995) *J. Invest. Dermatol.* 105:20S–24S; and Larsen, et al. (1989) *Immunology* 68:31–36), but are also broadly expressed outside this tissue (Rollins (1997) *Blood* 90:909–928).

To determine the cellular origin of CTACK, mRNA was looked for in cultured skin-derived cells that were either left untreated or treated with TNF-plus IL-1 for 6 h or 18 h. These pro-inflammatory cytokines are important primary regulators of immune responses in the skin and can induce the expression of other inflammatory mediators, including chemokines. Schroder (1995) *J. Invest. Dermatol.* 105:20S–24S; Larsen, et al. (1989) *Immunology* 68:31–36; and Goebeler, et al. (1997) *J Invest Dermatol* 108:445–451. CTACK message is detected in human keratinocytes, the predominant cell type in the epidermis, and is upregulated after 6 h or 18 h cytokine treatment. Competitive RT-PCR analysis confirms this result and demonstrates up to a 30-fold induction in CTACK message. In contrast, other skin-derived cell types such as melanocytes, T cells and dermal fibroblasts do not express CTACK under any of the conditions tested. These experiments show that CTACK message is expressed constitutively but can also be upregulated by inflammatory signals.

The regulated, skin-specific expression of CTACK makes it an excellent candidate for selective recruitment of skin-homing memory T cells. The ability of CTACK to chemoattract different T cell subsets was evaluated.

Extensive quantitative PCR methods have been applied, expression of the human GPR2 is particularly high in pooled heavy smoker lung samples, and dendritic cells from monocytes, activated by IL-4 and LPS. Very high amounts were detected in normal human lung samples, activated dendritic cells, activated MOT72 cell line, activated or resting JY B cell line, fetal ovary, fetal adipose tissue, fetal gall bladder, eosinophils, resting PBMC, and others.

Most abundant expression of CTACK was observed in keratinocytes of the basal layers of the epidermis. Upon normal differentiation keratinocytes of suprabasal layers appear to produce lower amounts of CTACK protein. Non-lesional skin of atopic dermatitis or psoriatic patients display a similar expression pattern. Within acute or chronic skin lesions of atopic dermatitis or psoriatic patients, however, suprabasal keratinocytes also exhibit strong CTACK expression, while immunohistochemical analyses using isotype control antibodies were uniformly negative. Basal keratinocytes secrete large amounts of CTACK protein into the papillary dermis. Next to basal keratinocytes, CTACK reactivity on extracellular matrix, fibroblasts, and dermal endothelial cells of the superficial plexus was detected. Endothelial cells of the superficial dermal plexus displayed CTACK both on their abluminal as well as luminal sites. This phenomenon was more pronounced in inflamed versus nonlesional or normal skin. The lack of detectable CTACK transcripts in cultured resting or activated dermal fibroblasts or dermal microvascular endothelial cells, indicates that CTACK may be actively secreted into the papillary dermis and immobilized on extracellular matrix and on the surface of endothelial cells.

VI. Chemotaxis.

Recombinant mouse CTACK was produced in *E. coli* and purified by R&D Systems as previously described for other chemokines. Hedrick, et al. (1998) *Blood* 91:4242–4247. Total human T cells in DMEM, pH 6.9, 1% bovine serum albumin, were added to the top chamber of 3 μm pore polycarbonate Transwell culture insert (Costar) and incubated with the indicated concentrations of purified chemokine in the bottom chamber for 3 h. The number of migrating cells of each subtype was determined by multi-parameter flow cytometry using fluorochrome conjugated antibodies against CLA (HECA-452), CD4, CD8, and CD45RO (Pharmingen). A known number of 15 μm microsphere beads (Bangs Laboratories, Fishers, Ind.) was added to each sample before analysis in order to determine the absolute number of migrating cells. As an example, an average of 6272 CLA$^+$ cells migrated in response to the optimal concentration of CTACK compared with 666 cells with medium alone.

Chemotaxis assays were performed with purified human peripheral-blood T cells and skin-homing T cells were identified by their expression of CLA. Recombinant murine CTACK chemoattracts both CD4$^+$ and CD8$^+$ T cells that co-express CLA. In contrast, CLA$^-$ T cells, from both the CD4$^+$ and CD8$^+$ populations, do not significantly respond to CTACK. CLA$^+$ cells migrate only in the presence of a gradient of CTACK, indicating that the response is chemotactic and not nonspecifically chemokinetic. By comparison, 6Ckine, a known T-cell chemoattractant (Nagira, et al. (1997) *J. Biol. Chem.* 272:19518–19524; Hromas, et al. (1997) *J. Immunol.* 159:2554–2558; Hedrick and Zlotnik (1997) *J. Immunol.* 159:1589–1593), is not only a less potent attractant for CLA$^+$ T cells, but also lacks specificity for CLA$^+$ cells as it preferentially attracts CLA$^-$ cells. CTACK does not attract effectively human B cells or neutrophils. Lack of an anti-mouse CLA antibody precludes similar analysis in the mouse.

The CLA$^+$ memory T cell subset constitutes a skin-associated population of memory cells that preferentially extravasate at normal (Bos, et al. (1993) *Arch. Dermatol. Res.* 285:179–183) and chronically inflamed cutaneous sites (Picker, et al. (1990) *Am. J. Pathol.* 136:1053–1068). This subpopulation has been shown to be involved in local immunity and inflammatory cutaneous reactions. Santamaria Babi, et al. (1995) *Immunol. Res.* 14:317–324. It has been proposed that CLA targets memory T cells to cutaneous sites via interaction with its vascular ligand E-selectin. Picker, et al. (1991) *Nature* 349:796–799; and Berg, et al. (1991) *J. Exp. Med.* 174:1461–1466. However, neutrophils express CLA (De Boer, et al. (1994) *Immunology* 81:359–365) yet they do not preferentially migrate to skin. Furthermore, E-selectin is induced on inflamed endothelium in cutaneous and non-cutaneous sites. Therefore, CLA/E-selectin binding can not fully explain the skin-specific homing of CLA$^+$ memory T cells. Several chemokines are expressed in skin (Schroder (1995) *J. Invest. Dermatol.* 105:20S–24S) and may play a role in inflammation of this tissue (Larsen, et al. (1995) *J. Immunol.* 155:2151–2157; Santamaria Babi, et al. (1996) *Eur. J. Immunol.* 26:2056–2061; Sarris, et al. (1995) [see comments] *Blood* 86:651–658); however, these chemokines are broadly expressed (Rollins (1997) *Blood* 90:909–928). Here we describe a novel chemokine, CTACK, that is specifically expressed in skin and selectively chemoattracts CLA$^+$ skin-homing T cells. Together these data suggest that CTACK may provide the skin-specific cue directing recruitment of CLA$^+$ memory T cells to cutaneous sites and provides a potential target to specifically regulate T cell trafficking to the skin. Similar assays can be performed with primate or rodent Vic.

VII. Antibody Production

Appropriate mammals are immunized with appropriate amounts of CTACK, Vic, GPR2, or gene transfected cells, e.g., subcutaneously every 2 weeks for 8 weeks. Typically, rodents are used, though other species should accommodate production of selective and specific antibodies. The final immunization is given intravenously (IV) through the tail vein.

Generic polyclonal antibodies may be collected. Alternatively, monoclonal antibodies can be produced. For example, four days after the IV injection, the spleen is removed and fused to SP2/0 and NS1 cells. HAT resistant hybridomas are selected, e.g., using a protocol designed by Stem Cell Technologies (Vancouver, BC). After 10 days of HAT selection, resistant foci are transferred to 96 well plates and expanded for 3 days. Antibody containing supernatants are analyzed, e.g., by FACS for binding to NIH3T3/surface CTACK transfectants. Many different CTACK mAbs are typically produced. Those antibodies may be isolated and modified, e.g., by labeling or other means as is standard in the art. See, e.g., Harlow and Lane (1988) *Antibodies: A Laboratory Manual* CSH Press; Goding (1986) *Monoclonal Antibodies: Principles and Practice* (2d ed.) Academic Press, New York, N.Y. Methods to conjugate magnetic reagents, toxic entities, labels, attach the antibodies to solid substrates, to sterile filter, etc., are known in the art.

VIII. Purification of Cells

CTACK or Vic responsive cells may be identified using the reagents described herein. For example, cells which are chemoattracted towards CTACK or Vic may be purified from other cells by collecting those cells which traverse towards CTACK or Vic. Such chemotaxis may be to a source of chemokine, or may be across a porous membrane or other substrate. See above, in the microchemotaxis assay.

Analysis of human samples can be evaluated in a similar manner. A biological sample, e.g., blood, tissue biopsy sample, lung or nasal lavage, skin punch, is obtained from an individual suffering from a skin related disorder. CTACK or Vic responsive cell analysis is performed, e.g., by FACS analysis, or similar means.

IX. Antagonists

Various antagonists of CTACK or Vic are made available. For example, antibodies against the chemokine itself may block the binding of ligand to its receptor, thereby serving as a direct receptor antagonist. Other antagonists may function by blocking the binding of ligand to receptor, e.g., by binding to the ligand in a way to preclude the possibility of binding to the receptor. Other antagonists, e.g., mutein antagonists, may bind to the receptor without signaling, thereby blocking a true agonist from binding. Many of these may serve to block the signal transmitted to target cells, specifically CTACK- or Vic-responsive cells. These may be skin cells, including Langerhans, fibroblasts, or keratinocytes. In particular, the matching to receptor indicates that certain antibodies against ligand interacting epitopes of the GPR2 receptor should block ligand binding.

Information on the criticality of particular residues is determined using standard procedures and analysis. Standard mutagenesis analysis is performed, e.g., by generating many different variants at determined positions, e.g., at the positions identified above, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analyzed, e.g., by PCR analysis and sequencing. This allows evaluation of population polymorphisms.

X. Immunohistochemistry

Frozen 6 $\mu$m tissue sections, from punch biopsies of patients with either lesional and nonlesional skin of psoriatic, atopic dermatitis, and allergic contact dermatitis patients, or from normal healthy individuals, were fixed in acetone and immunostaining was performed as described in Homey, B., et al. (2000) *J Immunol.* 164, 6621–6632 (2000); and Muller, A. et al. (2001) *Nature* 410, 50–56. (2001).

Serial sections were stained with mouse anti-human CTACK (124302; IgG2a, R&D Systems Inc., Minnesota, Minn.), mouse anti-human CCR10 (1908; IgG1; DNAX Research Institute; Palo Alto, Calif.), rat anti-human CD3 (CD3–12; IgG1; Serotec, Raleigh, N.C.) and mouse anti-human CD31 (JC/70A, IgG1, Dako, Glostrup, Denmark) mouse monoclonal antibodies. For immunostaining in mice, rat anti-mouse CTACK mAb (68706, IgG2a; R&D Systems) or rat anti-mouse CD3 (IgG, Serotec) were used. The binding of mouse or rat IgG was detected using alkaline phosphatase-conjugated or biotinylated rabbit anti-mouse or rat IgG followed by streptavidin-peroxidase (Vectastain ABC kit: mouse or rat IgG PK-4005: Vector, Burlingame, Calif.), respectively. The phospatase or peroxidase activities were revealed using alkaline phosphatase substrate III (SK-5300, Vector) or 3-amino-9-ethylcarbazole (AEC) substrate (SK-4200, Vector), respectively. Negative controls were established by adding appropriate non-specific isotype controls (R&D Systems) as primary antibodies.

Immunohistochemical analyses of CCR10 expression in skin of healthy individuals revealed that no CCR10 positive cells were dectable within the epidermis and only scattered expression of CCR10 appeared on cells confined to the superficial dermal plexus. In contrast, lesional skin of patients suffering from psoriasis or atopic dermatitis showed strong CCR10 expression on skin-infiltrating dermal leukocytes and intraepidermal lymphocytes. Staining of CD3 in serial sections of lesional atopic dermatitis and psoriatic skin indicated that the majority of skin-infiltrating lymphocytes were CCR10 positive. Furthermore, we detected no significant difference in the relative number of $CCR10^+$ skin-infiltrating leukocytes in lesions of psoriatic skin, acute or chronic dermatitis lesions as well as lesions of allergic contact dermatitis.

Analyses in normal or nonlesional skin revealed that next to hematopoietic cells, stromal cells such as dermal fibroblasts and dermal microvascular endothelial cells also express CCR10. These findings are in line with previous observations showing CCR10-specific transcripts in dermal fibroblasts and dermal microvascular endothelial cells and an absence of CCR10-specific mRNA in epidermal keratinocytes which instead are a potent and specific source of CTACK mRNA. Taken together, the distinct patterns of CTACK and CCR10 expression in normal versus inflamed skin were consistent in skin from five healthy donors, seven donors of nonlesional or lesional psoriatic and nine donors of non-lesional or lesional atopic dermatitis skin. No marked differences in CTACK and CCR10 expression were observed in lesional skin of psoriatic or atopic dermatitis patients. Furthermore, acute or chronic lesions showed no apparent differences in protein expression, however, the level of CTACK and CCR10 protein expression correlated with the clinical severity of the lesions as well as the amount of inflammatory infiltrate.

A. Dynamic Expression of Human CTACK and CCR10 During the Elicitation of Allergen-specific Inflammatory Skin Responses.

To study the expression of CTACK and CCR10 during the dynamic process of inflammation-induced leukocyte recruitment to the skin, skin biopsies of patch test reactions of nickel allergy patients were analyzed before and 6, 24 or 48 hours following topical allergen exposure. Untreated skin of nickel contact dermatitis patients showed a comparable CTACK and CCR10 expression pattern as normal skin of healthy volunteers. Strong expression of CTACK was observed in basal keratinocytes and additional CTACK reactivity could be detected on dermal endothelial cells of the superficial plexus. Six hours after nickel exposure, epidermal keratinocytes of basal and suprabasal layers of the skin increased CTACK production and abundant CTACK production and secretion into the dermis were detected 24 hours following hapten exposure.

Unexposed skin showed weak and scattered expression of CCR10 within the dermis. Co-localization studies on serial sections indicated that weak CCR10 expression within the dermis matched with the presence of CD31-positive endothelial cells of the superficial dermal plexus. Six hours after hapten exposure, dermal CCR10 reactivity confined to dermal vascular structures increased and developed into strong CCR10-positive perivascular, subepidermal and intraepidermal infiltrates 24 and 48 hours afterwards. Staining of serial sections with either anti-CCR10 or anti-CD3 antibodies indicated that over 90% of the skin-infiltrating lymphocytes were CCR10-positive. Strongest CCR10 expression was observed on the surface of perivascular lymphocytes. Notably, also epidermis-infiltrating lymphocytes showed strong CCR10 expression in nickel-challenged human skin.

B. CCR10 is Expressed on a Subset of Circulating Skin-homing T Cells

Immunohistochemical evaluation of inflamed skin shows that the vast majority (>90%) of skin-infiltrating lymphocytes are CCR10 positive. The distribution of CCR10 on circulating skin-homing T cells was also investigated. Flow cytometric analyses indicated that CCR10 is expressed on a subset of $CLA^+$ memory $CD4^+$ and $CD8^+$ T cells. Comparing CCR10 expression on $CD4^+/CLA^+$ T cells of 5 different healthy donors, approximately 30–40% of all $CD4^+$ circulating skin-homing $CLA^+$ T cells express CCR10. Besides skin-homing T cells, CCR10 immunohistochemistry as well as RNA analyses suggested that dermal fibroblast and dermal microvascular endothelial cells express this receptor on their surface. Staining of cultured primary dermal microvascular endothelial cells and dermal fibroblasts confirmed strong CCR10 expression on the surface of those non-hematopoietic cells in vitro.

C. Pro-inflammatory Stimuli Induce CTACK Production in Keratinocytes

Immunohistochemical results indicated that CTACK is a homeostatic chemokine whose expression is regulated by the differentiation stage of its cell of origin and by inflammatory processes. In vitro, cultured primary as well as transformed keratinocytes show increased levels of CTACK mRNA after stimulation with TNF-α/IL-1β, however, exposure to IL-4 or IFN-γ did not affect mRNA expression (see, e.g., Homey et al. supra).

CTACK protein production was increased within the cytoplasm of TNF-α/IL-1β stimulated PAM212 cells using confocal microscopy. Furthermore, enzyme-linked immunosorbent assays specific for either human or mouse CTACK confirmed these findings at the protein level. Twenty-four hour supernatants of resting transformed murine keratinocytes (PAM212 cells) or human primary keratinocytes showed low levels of CTACK protein, respectively. However, stimulation with TNF-α/IL-1β resulted in a 3–6 fold up-regulation of CTACK protein. Additional IL-10 treatment did not result in significant suppression of mCTACK production by transformed mouse keratinocytes, but reduced hCTACK secretion in human primary keratinocytes. In addition, IL-4 or IFN-γ treatment did not markedly induce mouse or human CTACK protein.

XI. Cell Culture

Human primary epidermal keratinocytes, dermal fibroblasts and dermal microvascular endothelial cells were purchased from Clonetics (San Diego, Calif.) and cultured in keratinocyte (KGM), fibroblast (FGM) and endothelial cell (EGM) growth medium as described (see, e.g., Homey et al. supra.) Cells were treated with human TNF-α (10 ng/ml)/IL-1β (5 ng/ml), IL-10 (10 ng/ml), IFN-γ (20 ng/ml), IL-4 (50 ng/ml) (R&D Systems) or left untreated. Mouse PAM212 keratinocytes were cultured in DMEM plus 10% fetal calf serum and stimulated with mouse TNF-α (10 ng/ml)/IL-1β (5 ng/ml), IFN-γ (20 ng/ml), IL-4 (50 ng/ml) or IL-10 (10 ng/ml) (R&D Systems). Supernatants as well as cells were harvested after six or 24 hours.

XII. ELISA

For the detection of mouse CC27, the rat anti-mouse CTACK mAb (68623.111; IgG2b) served as a capture antibody and biotinylated goat anti-mouse CTACK polyclonal antibodies (IgG) were used to reveal the captured mCTACK. In parallel, anti-human CTACK mAb (124302.11, IgG2a) captured and biotinylated goat anti-human CTACK polyclonal antibodies (IgG) were used to reveal the captured hCTACK. Recombinant mouse or human CTACK protein was used for standard curves (all reagents from R&D Systems).

XIII. FACS Analysis and Confocal Microscopy

To analyze CCR10 expression on skin-homing T cell subsets, PBMCs were isolated and stained for CLA, CD4, CD8 and CCR10 using the following antibodies: FITC-conjugated anti-CLA (HECA452) mAb, APC-conjugated anti-CD8 (RPA-T8), Cy-chrome-conjugated anti-CD4 (RPA-T4) (Pharmingen, San Diego, Calif.), anti-hCCR10 (Clone #1908; mouse IgG1; DNAX Research Institute). Briefly, $10^6$ PBMCs were stained with anti-CD4, anti-CD8, anti-CLA, anti-CCR10 mAb or isotype controls and analyzed using a FACSCalibur and CELLQuest software (Becton Dickinson, San Jose, Calif.). To analyze CCR10 expression on non-hematopoietic cells, cultured primary dermal fibroblasts and dermal microvascular endothelial cells were stained with anti-hCCR10 (1908; mouse IgG1; DNAX Research Institute; Palo Alto, Calif.) and cell surface expression was determined using flow cytometry. Mouse PAM212 keratinocytes were treated with brefeldin for 24 hours, harvested, fixed, permeabilized and stained with anti-mCTACK mAb (68623, rat IgG2b, R&D Systems) or isotype control. As a secondary antibody FITC conjugated rabbit anti-mouse IgG (Pharmingen) was used. Subsequently, cells were analyzed by confocal microscopy (LeicaDMR).

XIV. CTACK Binding and T Cell Adhesion Assays.

Cultured primary dermal microvascular endothelial cells and dermal fibroblast were incubated with chemically synthesized and biotinylated human CTACK protein (1–400 nM) (Gryphon Sciences, South San Francisco) for 30 min, washed twice, stained with PE-conjugated streptavidin and CTACK binding was analyzed using flow cytometry. In separate experiments 200 nM biotinylated CTACK competed increasing concentrations (1–400 nM) of either CXCL8 or CCL5 for cell surface binding.

Binding studies using biotinylated human CTACK protein confirmed that this CC chemokine interacts with the surface of dermal microvascular endothelial cells and fibroblasts. Competition studies indicated that CCL5 as well as CXCL8 are able to interfere with CTACK binding to cell surfaces in a dose dependent manner suggesting that the dominant binding partners for CTACK are glycosaminoglycans rather than CCR10. Sequestered on dermal endothelial cells, CTACK may mediate firm adhesion and transendothelial migration of circulating CCR10+ leukocytes.

XV. Cutaneous Injection of CTACK

Flanks of BALB/c mice were shaved and intradermally injected with either recombinant human CTACK (0.2, 2, 20 μg) at the ipsilateral or PBS on the contralateral site. In parallel experiments 4 μg of recombinant mouse CTACK was injected. Skin was harvested 48 hours after injection and used for RNA extraction and immunohistochemistry.

To determine the chemoattractive properties of recombinant CTACK protein in vivo, BALB/c mice were injected intradermally with either recombinant human CTACK protein (0.2, 2, 20 μg) or PBS into the ipsi- or contralateral flank of five mice per group, respectively. Real time quantitative RT-PCR analyses revealed that CTACK injection induced the expression of the T cell specific cytokine IL-2, the CTACK receptor CCR10 and the α-chain of the lymphocyte function associated antigen-1 (LFA-1α) in a dose dependent manner, indicating an increased recruitment of T lymphocytes to sites of injection. Notably, transcripts for the T cell receptor β-chain also showed a 3–6 fold upregulation after CTACK treatment. In parallel, histological analyses following intracutaneous injection of 4 μg of mCTACK protein confirmed the increased number of CD3+ lymphocytes to sites of CTACK injection.

XVI. Real Time Quantitative RT-PCR

Homogenization of skin biopsies, RNA extraction and real time quantitative PCR was performed as described (see, Homey et al. supra; and Muller, et al. supra). Primer and probe pairs specific for mCTACK and mCCR10 were obtained from Applied Biosystems (Foster City, Calif.). The following other primer pairs were used: LFA-1 α-chain, IL-2, and T cell receptor β-chain. Gene-specific PCR products were measured by means of an ABI PRISM® 7700 Sequence Detection System (Applied Biosystems). Target gene expression was normalized between different samples based on the values of the expression of ubiquitin or ribosomal 18S RNA.

XVII. Contact Hypersensitivity

Ten BALB/c mice were treated with 0.5% di-nitrofluorobenzene (DNFB) on the shaved abdomen. On day five and six, mice received intraperitoneal injections (1 mg/mouse) of neutralizing antibodies against mCTACK (68623, rat IgG2b, R&D Systems). Two hours after the second i.p. injection, mice were challenged with 0.2% of DNFB on the left ear and ear swelling was monitored after 24, 48 and 72 hours using a spring-loaded micrometer (Oditest, Kröplin, Schlüchtem, Germany). Non-sensitized animals were challenged with 0.2% DNFB and used as controls. Ears were harvested for routine histology and immunohistochemistry.

XVIII. Adoptive Transfer Experiments

Ten BALB/c mice were treated with 0.5% di-nitrofluorobenzene (DNFB) on the dorsal and ventral surfaces of both ears. On day five, auricular lymph nodes and spleens were harvested, pooled, and stained with the vybrant CFDA, SE cell tracer kit (CFSE; Molecular Probes; Eugene, Oreg.). Subsequently, $5 \times 10^7$ cells were injected into the tail vein of naive recipient mice which had been treated with intraperitoneal injections of neutralizing anti-mCTACK (68623, rat IgG2b, R&D Systems) or isotype 24 and 2 hours prior to challenge with contact allergen (0.2% DNFB). Ear swelling was monitored at 24, 48 and 72 hours. In other experiments, mice were sacrificed twenty-four hours after challenge and skin-infiltrating leukocytes were extracted using collagenase digestion as described (see, e.g., Hong, et al. (1999) *J. Immunol.* 162:7480–7491). In order to calculate the number of skin-infiltrating CFSE-positive cells per ear, 100,000 15 μm microsphere beads (Bangs Laboratories, Fishers, Ind.) were added during the extraction procedure and cells were measured using flow cytometry.

XIV. Neutralization of CTACK/CCR10 Interactions Impairs Leukocyte Recruitment to Allergen-challenged Skin The pathological role of CTACK/CCR10 interaction in cutaneous inflammation and its functional relevance as a therapeutic target in vivo was investigated. Given the dynamic expression of CTACK and its receptor CCR10 during the elicitation of contact allergy in nickel contact dermatitis patients, a pathogenically relevant contact hypersensitivity model for in vivo proof-of-principle studies was chosen. Elicitation of DNFB-specific skin inflammation in mice indicated that CTACK is constitutively present in normal keratinocytes but upregulated upon inflammation. To obtain further insights into the regulation of CTACK in vivo, ears of BALB/c mice were topically treated with a strong glucocorticosteroid (0.3% clobetasol propionate) an known therapeutic for inflammatory or autoimmune skin disease. Immunohistochemical evaluation showed that CTACK expression was markedly suppressed after clobetasol treatment when compared to vehicle-treated controls.

Among a panel of monoclonal antibodies directed against mCTACK, we identified a clone (#68623, rat IgG2b) which neutralized mCTACK-induced intracellular $Ca^{2+}$ mobilization and chemotaxis of human and mouse CCR10-transfected BAF/3 cells.

To study the effects of the neutralization of mCTACK on the recruitment of pathogenically relevant cells into the skin, BALB/c mice were sensitized with the potent contact allergen di-nitrofluorobenzene (DNFB), treated with either neutralizing antibodies against mCTACK or isotype control and subsequently challenged with 0.2% DNFB on the ear. Histological analyses indicated a markedly reduced skin thickness in anti-mCTACK-treated mice which showed only slight perivascular infiltrates but little or no epidermal leukocyte recruitment. Monitoring of challenge-induced ear swelling (24–72 hours) confirmed a significant suppression of skin inflammation in anti-mCTACK-treated mice when compared to mice injected with an isotype control (p<0.01). Relative suppression of ear swelling in five independent experiments ranged between 60–85%. In additional experiments, anti-mCTACK treatment provided superior inhibition of contact allergen-induced skin inflammation compared to pre-treatments with the topical immunosuppressant tacrolimus/FK506 (1%). Notably, topical tacrolimus treatment shows strong clinical efficacy in patients suffering from atopic dermatitis.

To monitor the effects of CTACK/CCR10 neutralization on allergen-induced recruitment of lymphocytes into the skin, draining lymph node and spleen cells of sensitized BALB/c mice were labeled with CFSE (carboxyfluorescein diacetate, succinimidyl ester) and adoptively transferred into naïve mice, pretreated with neutralizing anti-mCTACK or isotype before contact allergen challenge. Ear swelling measurements indicated that neutralization of mCTACK significantly impaired allergen-specific skin inflammation in this adoptive transfer. Moreover, extraction and quantification of skin-infiltrating $CFSE^+$ lymphocytes from allergen challenged mouse ears showed that anti-mCTACK treated mice have an average of 37% less $CFSE^+$ skin-infiltrating lymphocytes compared to isotype-treated control animals. Further analyses using a total lymphocyte gate indicated that anti-mCTACK treated mice who received adoptively transferred cells show on average 31% lymphocytes present in the skin compared to isotype-treated control mice. These results show that neutralization of CTACK/CCR10 interactions in vivo impairs lymphocyte recruitment to the skin and leads to the inhibition of allergen-induced skin inflammation.

All citations herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method for impairing movement of a cutaneous lymphocyte-associated antigen+ (CLA+) memory T-cell within or to the skin of a mammal, said method comprising administering to said mammal an effective amount of an antibody against cutaneous-T-cell-attracting chemokine (CTACK), whereby administration of said antibody impairs movement of said cutaneous lymphocyte-associated antigen memory T-cell within or to the skin of said mammal.

2. The method of claim 1, wherein said movement is within said skin.

3. The method of claim 1, wherein said antibody neutralizes cutaneous-T-cell-attracting chemokine.

4. A method for treating a patient suffering from a skin disorder selected from the group consisting of allergic-contact dermatitis and psoriasis comprising administering an effective amount of an antibody against cutaneous-T-cell-attracting chemokine.

5. The method of claim 1, wherein said administering is local.

6. The method of claim 1, wherein said cutaneous lymphocyte-associated antigen+ memory T-cell moves into the dermis or epidermis of said skin.

7. The method of claim 4, wherein said skin disorder is allergic-contact dermatitis.

8. The method of claim 4, wherein said skin disorder is psoriasis.

9. The method of claim 1, wherein said administering is systemic.

10. The method of claim 1, wherein said administering is topical.

11. The method of claim 1, wherein said administering is subcutaneous.

12. The method of claim 1, wherein said administering is intradermal.

13. The method of claim 1, wherein said administering is transdermal.

* * * * *

UNITED STATES PATENT AND TRADEMARK OFFICE
CERTIFICATE OF CORRECTION

PATENT NO. : 6,824,781 B2
DATED : July 2, 2001
INVENTOR(S) : Wei Wang et al.

It is certified that error appears in the above-identified patent and that said Letters Patent is hereby corrected as shown below:

<u>Title page, Item [54] and Column 1, Line 2,</u>
Title, change "MEMEORY" to -- MEMORY --.

<u>Title page,</u>
Item [60], Related U.S. Application Data, change "60/113,868" to -- 60/113,858 --.

<u>Column 69,</u>
Line 8, change "antigen" to -- antigen+ --.

Signed and Sealed this

Nineteenth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,824,781 B2 Page 1 of 1
APPLICATION NO. : 09/898751
DATED : July 2, 2001
INVENTOR(S) : Wei Wang et al.

It is certified that error appears in the above-identified patent and that said Letters Patent is hereby corrected as shown below:

Title Page item 54 (title) and col. 1: change "MEMEORY" to --MEMORY--.

Title Page item 60 (Related U.S. Application Data): change "60/113,868" to --60/113,858--.

Column 69, line 8 (claim 1): change "antigen" to --antigen+--.

Signed and Sealed this

Seventh Day of October, 2008

JON W. DUDAS
*Director of the United States Patent and Trademark Office*

UNITED STATES PATENT AND TRADEMARK OFFICE
CERTIFICATE OF CORRECTION

PATENT NO. : 6,824,781 B2  Page 1 of 1
APPLICATION NO. : 09/898751
DATED : November 30, 2004
INVENTOR(S) : Wei Wang et al.

It is certified that error appears in the above-identified patent and that said Letters Patent is hereby corrected as shown below:

Title Page item 54 (title) and col. 1: change "MEMEORY" to --MEMORY--.

Title Page item 60 (Related U.S. Application Data): change "60/113,868" to --60/113,858--.

Column 69, line 8 (claim 1): change "antigen" to --antigen+--.

This certificate supersedes the Certificates of Correction issued April 19, 2005 and October 7, 2008.

Signed and Sealed this

Twenty-first Day of October, 2008

JON W. DUDAS
*Director of the United States Patent and Trademark Office*